US005945569A

United States Patent [19]
Miki et al.

[11] Patent Number: 5,945,569

[45] Date of Patent: Aug. 31, 1999

[54] CATALYST AND METHOD FOR PRODUCING PHENOLS

[75] Inventors: Jun Miki; Minoru Asanuma; Takeshi Konishi; Yakudo Tachibana; Tsutomu Shikada, all of Kawasaki-ku; Aiko Watanabe, Fujisawa, all of Japan

[73] Assignee: NKK Corporation, Tokyo, Japan

[21] Appl. No.: 08/649,931

[22] Filed: May 16, 1996

Related U.S. Application Data

[62] Division of application No. 08/274,970, Jul. 14, 1994, abandoned.

[30] Foreign Application Priority Data

Aug. 20, 1993 [JP] Japan .................................... 5-206503

[51] Int. Cl.[6] .................................................... C07C 37/00

[52] U.S. Cl. ............................................................ 568/801

[58] Field of Search .................................... 568/716, 801, 568/802; 502/335, 336

[56] References Cited

U.S. PATENT DOCUMENTS

| | | | |
|---|---|---|---|
| 3,926,853 | 12/1975 | Senes et al. . | |
| 4,060,545 | 11/1977 | Miller et al. | 560/208 |
| 4,390,736 | 6/1983 | Inoue et al. | 568/801 |
| 4,620,043 | 10/1986 | Lam et al. | 568/801 |
| 5,268,512 | 12/1993 | Miki et al. | 502/330 |

FOREIGN PATENT DOCUMENTS

| | | |
|---|---|---|
| 0 052 839 | 6/1982 | European Pat. Off. . |
| 0 226 640 | 7/1987 | European Pat. Off. . |
| 0 452 695 | 10/1991 | European Pat. Off. . |
| 0 538 912 | 4/1993 | European Pat. Off. . |
| 57-11932 | 1/1982 | Japan . |
| 4-277029 | 10/1992 | Japan . |
| 59-20384 | 5/1994 | Japan . |

OTHER PUBLICATIONS

M. Hronec et al, Oxidation of Benzoic Acid to Phenol in The Vapor Phase III. Reaction of Phenol Precursors Over Copper Catalysts, Applied Catalysis, 69 (1991) pp. 201–204, Elsevier Science Publishers B.V., Amsterdam.

*Primary Examiner*—Michael L. Shippen
*Attorney, Agent, or Firm*—Frishauf, Holtz, Goodman, Langer & Chick, P.C

[57] ABSTRACT

A catalyst for producing phenols consists essentially of;

an iron oxide;

a nickel oxide;

at least one first oxide selected from the group consisting of a vanadium oxide and a molybdenum oxide; and at least one second oxide selected from the group consisting of an alkali metal oxide and an alkaline earth metal oxide.

The catalyst is used to produce phenols from benzoic acid or an alkyl benzoic acid.

17 Claims, No Drawings

CATALYST AND METHOD FOR PRODUCING PHENOLS

This application is a Division of application Ser. No. 08/274,970, filed Jul. 14, 1994, now abandoned.

BACKGROUND OF THE INVENTION

1. Field of the Invention

The present invention relates to a catalyst for producing phenol or alkyl phenol and to a method for producing phenol or alkyl phenol by gas phase oxidation of benzoic acid or alkyl benzoic acid under the presence of the catalyst.

2. Description of the Related Art

Various methods and catalysts are known to produce phenol by gas phase contact oxidation of benzoic acid.

For example, JP-A-57-11932 (the term JP-A- referred to hereinafter signifies unexamined Japanese patent publication) disclosed a catalyst containing at least one of a copper compound, a vanadium compound, a silver compound, a lithium compound, a sodium compound, and a magnesium compound, and a method using the catalyst.

JP-B-59-20384 (the term JP-B- referred to hereinafter signifies examined Japanese patent publication) disclosed a method using a catalyst containing oxides of copper, zirconium, and alkali metal and being supported on $\alpha$-alumina. JP-B-64-934 disclosed a method using an oxide catalyst containing a variety of metallic elements: namely, molybdenum as the essential component, at least one of vanadium, niobium, and tantalum, and at least one of copper, silver, manganese, iron, cobalt, nickel, rhodium, palladium, and platinum, and at least one of thallium, an alkali metal, and an alkaline earth metal.

The inventors conducted extensive study on the catalyst for phenol production and on the method for producing phenol, and provided the catalysts to produce phenol by gas phase contact oxidation of benzoic acid, which catalysts include the catalyst of a nickel compound supported on a metallic oxide such as titania, magnesia, and $\alpha$-alumina (JP-A-4-5250), the catalyst containing an iron oxide and a nickel oxide (JP-A-4-330944), the catalyst containing an iron oxide, a nickel oxide, and an alkali earth metal compound (JP-A-4-330945), the catalyst containing an iron oxide, a nickel oxide, and an alkali metal compound (JP-A-4-104837), the catalyst containing an iron oxide, a nickel oxide, an alkali metal compound, and an alkaline earth metal compound (JP-A-4-330946), and the catalyst containing a composite metallic oxide having a spinel crystal structure.

Furthermore, the inventors provided a catalyst to produce phenol by gas phase oxidation of toluene, which catalyst contains a vanadium oxide, an iron oxide, and a nickel oxide (JP-A-4-277029).

However, the catalyst disclosed in JP-A-57-11932 is insufficient in both activity and selectivity, and the method for producing phenol using the catalyst gives the conversion of benzoic acid of 50.5% and the selectivity to phenol of 88.6% at the maximum. In addition, when an exothermic reaction such as oxidation of benzoic acid is carried out using a catalyst containing a copper compound, the catalyst bed likely induces hot spots which raises a problem of sintering of the catalyst and of significant degradation of the activity. The method for producing phenol disclosed in JP-B-59-20384 also shows an insufficient conversion and selectivity giving the conversion of benzoic acid of 63.7% and the selectivity to phenol of 82.2% at the maximum. Furthermore, the method induces the yield of a large amount of by-products such as diphenyl oxide, which significantly degrades the catalyst activity. The method also has an industrial disadvantage of necessity of refining stage for produced phenol.

The method for producing phenol disclosed in JP-B-64-934 also gives the conversion of benzoic acid of 75% and the selectivity to phenol of 89% at the maximum, which values are insufficient for industrial application. The method also has a problem of catalyst degradation with time.

All the three of above described methods gives a low space time yield of phenol (production amount of phenol per unit catalyst volume per unit time) not higher than 100, so the productivity is poor, and the methods are inapplicable to industrial process.

Regarding the production of cresol from toluic acid, which was disclosed in JP-B-64-934, the catalyst activity and the selectivity are insufficient giving the conversion of 45% and selectivity to m-cresol of 81% for the reaction of p-toluic acid (4-methyl benzoic acid), and gives the conversion of 48% and the selectivity to m-cresol of 79% for the reaction of o-toluic acid (2-methyl benzoic acid). M. Hronec, et al. pointed out a difficulty for obtaining a high yield of cresol species in the reaction system using a catalyst containing Cu owing to the unstable intermediate reaction products (Applied Catalysis, 69 (1991) pp201–204). In addition, the method has the problem of significant degradation of catalyst activity and of low space time yield, which is similar to the problem in the case of synthesis of phenol from benzoic acid.

The catalysts which were presented by the inventors improved the above described problems and improved the conversion of benzoic acid and the selectivity to phenol. Nevertheless, the development of catalysts which further improve the catalyst life and which are applicable to other reaction systems such as the ones to obtain alkyl phenol such as cresol from alkyl benzoic acid at a high yield have been wanted.

SUMMARY OF THE INVENTION

It is an object of the present invention to provide a catalyst which gives a high conversion of benzoic acid and alkyl benzoic acid and a high selectivity to phenol and alkyl phenol for a long period with a high space time yield, and to provide a method for producing phenol and alkyl phenol using the catalyst.

The present invention provides a catalyst for producing phenols consisting essentially of;

- an iron oxide;
- a nickel oxide;
- at least one first oxide selected from the group consisting of a vanadium oxide and a molybdenum oxide; and
- at least one second oxide selected from the group consisting of an alkali metal oxide and an alkaline earth metal oxide.

Further, the present invention provides a method for producing phenols using a catalyst from a benzoic acid or an alkyl benzoic acid, the catalyst consisting essentially of;

- an iron oxide;
- a nickel oxide;
- at least one first oxide selected from the group consisting of a vanadium oxide and a molybdenum oxide; and
- at least one second oxide selected from the group consisting of an alkali metal oxide and an alkaline earth metal oxide.

DESCRIPTION OF THE PREFERRED EMBODIMENT

The ratio of nickel oxide to iron oxide ($NiO/Fe_2O_3$) in the catalyst is preferably in an approximate range of from 0.1 to 10.0 by weight, and most preferably from 0.3 to 5. When the ratio exceeds approximately 10.0 by weight, the yield of CO and $CO_2$ generated by complete combustion increases, and the selectivity to phenol or alkyl phenol decreases. When the ratio is lower than approximately 0.1, the yield of benzene or alkyl benzene becomes predominant, and the selectivity to phenol or alkyl phenol decreases.

The vanadium oxide is preferably vanadium pentoxide ($V_2O_5$), and may include vanadium monoxide (VO), vanadium trioxide ($V_2O_3$) and/or di-vanadium tetroxide ($V_2O_4$).

A preferable range of vanadium oxide content is approximately from 0.1 to 10 wt. %, most preferably from 0.5 to 5 wt. %. When the content of vanadium oxide is less than 0.1 wt. %, the selectivity to phenol or alkyl phenol significantly degrades with time. When the content of vanadium oxide is above 10 wt. %, the yield of CO and $CO_2$ generated by complete combustion increases.

The molybdenum oxide is preferably molybdenum trioxide ($MoO_3$), and may include molybdenum dioxide ($MnO_2$).

A preferable range of molybdenum oxide content is from 0.1 to 10 wt. %, most preferably from 0.5 to 5 wt. %. When the content of molybdenum oxide is less than 0.1 wt. %, the selectivity to phenol or alkyl phenol significantly degrades with time. When the content of molybdenum oxide is above 10 wt. %, the yield of CO and $CO_2$ generated by complete combustion increases.

Presence of either one of the vanadium oxide or the molybdenum oxide is sufficient, and the sum of the content of these two oxides in a range of from 0.1 to 10 wt. % offers a satisfactory catalyst performance. Most preferable range of content of the sum of these oxides is from 0.5 to 5 wt. %. When the content of the sum of these oxides is less than 0.1 wt. %, the selectivity to phenol or alkyl phenol significantly degrades with time. When the content is above 10 wt. %, the yield of CO and $CO_2$ generated by complete combustion increases.

Alkali metal oxide includes $Li_2O$, $Na_2O$, $K_2O$, $Rb_2O$, $Cs_2O$. Among them, the oxides of sodium and potassium are preferred because they yield less CO and $CO_2$ and give higher conversion of benzoic acid and alkyl benzoic acid.

A preferable range of alkali metal oxide content is approximately from 0.05 to 30 wt. %, most preferably from 0.05 to 10 wt. %. When the content of alkali metal oxide is less than 0.05 wt. %, the yield of CO and $CO_2$ increases and the selectivity to phenol or alkyl phenol significantly degrades. When the content of alkali metal oxide is above 10 wt. %, the conversion of benzoic acid and alkyl benzoic acid degrades.

Alkaline earth metal oxide includes MgO, CaO, SrO, BaO. Among them, the oxides of calcium are preferred because they yield less benzene and alkyl benzene and give higher conversion of benzoic acid and alkyl benzoic acid.

A preferable range of alkaline earth metal oxide content is approximately from 0.05 to 30 wt. %, most preferably from 0.05 to 10 wt. %. When the content of alkaline earth metal oxide is less than approximately 0.05 wt. %, the yield of CO and $CO_2$ increases and the selectivity to phenol or alkyl phenol degrades. When the content of alkaline earth metal oxide is above 30 wt. %, the conversion of benzoic acid and alkyl benzoic acid degrades, and the yield of benzene and alkyl benzene increases, and the selectivity to phenol and alkyl phenol degrades.

Presence of either one of the alkaline metal oxide or the alkali earth metal oxide is sufficient, or of both of them may be acceptable. The sum of the content of these two oxides in a range of from 0.05 to 30 wt. % is sufficient.

The catalyst of the present invention may contain various compounds, and it may be supported on a titanium oxide or silica support.

The preparation of the catalyst of the present invention may be carried out using a known method applied for that type of catalysts. For example, the applicable raw materials include the nitrate, carbonate, organic salt, halide, hydroxide, and oxide of iron, nickel, vanadium or molybdenum, and alkali metal or alkaline earth metal. The method for mixing the above-described compounds of iron, nickel, vanadium or molybdenum, and alkali metal or alkaline earth metal may be conducted by a known process of precipitation, kneading, or impregnation. For instance, a prepared gel mixture of iron hydroxide and nickel hydroxide is mixed with the compounds of vanadium or molybdenum, and alkali metal or alkaline earth metal, or mixed with their solution, followed by drying and calcining. Otherwise, the kneaded product of iron oxide and nickel oxide may be mixed with the compounds of vanadium or molybdenum, and alkali metal or alkaline earth metal. The mixed and calcined product of iron oxide and nickel oxide may be mixed with the compounds of vanadium or molybdenum, and alkali metal or alkaline earth metal. The mixed and calcined product of iron oxide and nickel oxide may be impregnated with the compound of vanadium or molybdenum, and alkali metal or alkaline earth metal. The iron oxide, nickel oxide, vanadium oxide or molybdenum oxide, and oxide of alkali metal or alkaline earth metal may be powdered to mix, followed by compression molding to form pellets.

The catalyst is preferably calcined in air or inert gas during the preparation stage after the mixing of iron oxide and nickel oxide and is crystallized to one or more of iron oxide, nickel oxide, and composite oxide of iron and nickel. Generally, when a catalyst prepared by a known method is further calcined at a temperature of approximately 600° C. or more, the specific surface area reduces and the catalyst activity degrades. However, within a temperature range of from approximately 600 to 900° C., the catalyst of the present invention reduces the specific surface area with the increase of calcining temperature, but the activity for yielding phenol and alkyl phenol increases, and gives a high conversion of benzoic acid and alkyl benzoic acid and a high selectivity to phenol and alkyl phenol. When the calcining temperature is lower than approximately 600° C., only the reaction to yield CO and $CO_2$ by complete combustion proceeds while generating very little phenol and alkyl phenol, and induces the deposition of carbon materials on the catalyst surface. When the calcining temperature exceeds approximately 900° C., the conversion of benzoic acid and alkyl benzoic acid becomes significantly low, and gives very slight amount of phenol and alkyl phenol generation.

The following is the method for producing phenol and alkyl phenol of the present invention.

The raw material is benzoic acid or mono-alkyl benzoic acid. The position of alkyl group substitution on mono-alkyl benzoic acid may be either one of ortho-, meta-, or para-position. The alkyl group preferably has 1 to 8 carbons, more preferably 1 to 5, and most preferably around 1 to 3. Examples of the substituted benzoic acid are toluic acid, ethyl benzoic acid, and iso-propylbenzoic acid.

According to the method of the present invention, oxygen is supplied along with the raw material benzoic acid or alkyl benzoic acid. The amount of oxygen may be at a theoretical quantity or more to the raw material benzoic acid or alkyl benzoic acid, and preferably in a range of from approximately 0.5 to 50 mole fold to the quantity of raw material. When the supply of oxygen exceeds approximately 50 mole fold, the complete oxidation of the raw material benzoic acid or alkyl benzoic acid is likely to occur. When the supply of oxygen is less than approximately 0.5 mole fold, sufficient conversion of benzoic acid or alkyl benzoic acid can not be attained.

The supplied oxygen may be in a form of molecular oxygen. Generally, however, air is used. The air may be diluted with an inert gas.

The reaction is usually conducted under the presence of water vapor. The water vapor supply is preferably in a range of from approximately 1 to 100 mole fold to the quantity of raw material benzoic acid or alkyl benzoic acid. When the supply of water vapor exceeds approximately 100 mole fold, the operation becomes uneconomical. When the supply of water vapor is less than approximately 1 mole fold, generally the selectivity of phenol and alkyl phenol decreases.

A preferable range of space velocity is in a range of from approximately 100 to 50000 $hr^{-1}$. When the space velocity is less than approximately 100 $hr^{-1}$, sufficient space time yield can not be obtained. When the space velocity exceeds approximately 50000 $hr^{-1}$ the conversion of benzoic acid and alkyl benzoic acid decreases.

A preferable range of reaction temperature is approximately from 200 to 600° C., most preferably from approximately 300 to 500° C. When the reaction temperature is above approximately 600° C., the selectivity of phenol and alkyl phenol decreases. When the reaction temperature is below approximately 200° C., the conversion of benzoic acid and alkyl benzoic acid decreases.

The reaction pressure is not specifically limited if only the supplied raw material maintains gaseous phase under the reaction condition. Nevertheless, the reaction pressure is at atmospheric pressure or at a slightly positive pressure.

The method of the present invention may use either one of the fixed bed unit or the fluidized bed unit.

EXAMPLE

Example 1

Iron nitrate ($Fe(NO_3)_3.9H_2O$) 200 g and nickel nitrate ($Ni(NO_3)_2.6H_2O$) 144 g were dissolved to ion exchanged water 500 ml. Sodium hydroxide of approximately 100 g was dissolved to ion exchanged water 500 ml. Both solutions were added dropwise to an ion exchanged water 2 liter at room temperature while maintaining the pH in a range of from 7 to 8. After completing the dropwise addition, the resulted solution was agitated for approximately 1 hr. The generated precipitate was filtered and washed.

The obtained gel was mixed with aqueous solution 100 ml containing sodium carbonate ($Na_2CO_3.10H_2O$) 2.24 g, and the mixture was agitated for approximately 1 hr. The gel was dried in air at 120° C. for 24 hrs., followed by calcining in air at 800° C. for 4 hrs.

The calcined product was put into an aqueous solution prepared by dissolving ammonium methavanadate ($NH_4VO_3$) 2 g and oxalic acid ($(COOH)_2$) 4 g. The mixture was evaporated to dry, followed by drying at 120° C. for 24 hrs. and calcining at 500° C. for 3 hrs. to obtain the catalyst.

The catalyst had the composition of $Fe_2O_3$:NiO:$Na_2O$:$V_2O_5$=50.3:47.1:0.6:2.0 (by weight).

Examples 2–8

Catalysts containing several levels of vanadium oxide content were prepared by the same procedure with that in Example 1. The obtained catalysts were used in Examples 111 to 117, and the compositions are listed in Tables 7 and 8.

Examples 9–15

Catalysts containing several levels of sodium oxide content were prepared by the same procedure with that in Example 1. The obtained catalysts were used in Examples 118 to 124, and the compositions are listed in Tables 9 and 10.

Examples 16–20

Catalysts containing several levels of vanadium oxide content and sodium oxide content were prepared by the same procedure with that in Example 1. The obtained catalysts were used in Examples 125 to 129, and the compositions are listed in Table 11.

Examples 21–26

Catalysts containing several levels of composition ratio of $Fe_2O_3$ to NiO were prepared by the same procedure with that in Example 1. The obtained catalysts were used in Examples 130 to 135, and the compositions are listed in Tables 12 and 13.

Examples 27–31

Catalysts were prepared by the same procedure with that in Example 1 except for varying the calcining temperature of $Fe_2O_3$—NiO—$Na_2O$ before supporting the vanadium component. The obtained catalysts were used in Examples 136 to 140, and the compositions are listed in Table 14.

Example 32

Iron nitrate ($Fe(NO_3)_3.9H_2O$) 200 g and nickel nitrate ($Ni(NO_3)_2.6H_2O$) 144 g were dissolved to ion exchanged water 500 ml. Sodium hydroxide of approximately 100 g was dissolved to ion exchanged water 500 ml. Both solutions were added dropwise to an ion exchanged water 2 liter at room temperature while maintaining the pH in a range of from 7 to 8. After completing the dropwise addition, the solution was agitated for approximately 1 hr. The generated precipitate was filtered and washed.

The obtained gel was mixed with aqueous solution 100 ml containing sodium carbonate ($Na_2CO_3.10H_2O$) 3.68 g, and the mixture was agitated for approximately 1 hr. The gel was dried in air at 120° C. for 24 hrs., followed by calcining in air at 800° C. for 4 hrs.

The calcined product was put into an aqueous solution prepared by dissolving ammonium molybdate $(NH_4)_6Mo_7O_{24}.4H_2O$) 2.93 g. The mixture was evaporated to dry, followed by drying at 120° C. for 24 hrs. and calcining at 500° C. for 3 hrs. to obtain the catalyst.

The catalyst had the composition of $Fe_2O_3$:NiO:$Na_2O$:$MoO_3$=49.6:46.4:1.0:3.0 (by weight).

Examples 33–38

Catalysts containing several levels of molybdenum oxide content were prepared by the same procedure with that in Example 32. The obtained catalysts were used in Examples 141 to 147, and the compositions are listed in Tables 15 and 16.

Examples 39–45

Catalysts containing several levels of sodium oxide content were prepared by the same procedure with that in Example 32. The obtained catalysts were used in Examples 148 to 154, and the compositions are listed in Tables 17 and 18.

Examples 46–50

Catalysts containing several levels of molybdenum oxide content and sodium oxide content were prepared by the same procedure with that in Example 32. The obtained catalysts were used in Examples 155 to 159, and the compositions are listed in Table 19.

Examples 51–56

Catalysts containing several levels of composition ratio of $Fe_2O_3$ to NiO were prepared by the same procedure with that in Example 32. The obtained catalysts were used in Examples 160 to 165, and the compositions are listed in Tables 20 and 21.

Examples 57–61

Catalysts were prepared by the same procedure with that in Example 32 except for varying the calcining temperature of $Fe_2O_3$—NiO—$Na_2O$ before supporting the molybdenum component. The obtained catalysts were used in Examples 166 to 170, and the compositions are listed in Table 22.

Example 62

Iron nitrate ($Fe(NO_3)_3.9H_2O$) 200 g and nickel nitrate ($Ni(NO_3)_2.6H_2O$) 144 g were dissolved to ion exchanged water 500 ml. Sodium hydroxide of approximately 100 g was dissolved to ion exchanged water 500 ml. Both solutions were added dropwise to an ion exchanged water 2 liter at room temperature while maintaining the pH in a range of from 7 to 8. After completing the dropwise addition, the solution was agitated for approximately 1 hr. The generated precipitate was filtered and washed.

The obtained gel was mixed with aqueous solution 100 ml containing sodium carbonate ($Na_2CO_3.10H_2O$) 3.70 g, and the mixture was agitated for approximately 1 hr. The gel was dried in air at 120° C. for 24 hrs., followed by calcining in air at 800° C. for 4 hrs.

The calcined product was put into an aqueous solution 25 ml prepared by dissolving ammonium methavanadate ($NH_4VO_3$) 2.06 g and oxalic acid ($(COOH)_2$) 4 g and an aqueous solution 25 ml prepared by dissolving ammonium molybdate $(NH_4)_6Mo_7O_{24}.4H_2O$) 1.47 g. The mixture was evaporated to dry, followed by drying at 120° C. for 24 hrs. and calcining at 500° C. for 3 hrs. to obtain the catalyst.

The catalyst had the composition of $Fe_2O_3:NiO:Na_2O:V_2O_5:MoO_3$=49.3:46.2:1.0:2.0:1.5 (by weight).

Examples 63–71

Catalysts containing several levels of vanadium oxide content and molybdenum oxide content were prepared by the same procedure with that in Example 69. The obtained catalysts were used in Examples 172 to 180, and the compositions are listed in Tables 23 to 25.

Example 72

Catalyst containing potassium carbonate ($K_2CO_3$) 0.71 g instead of sodium carbonate 2.24 g was prepared by the same procedure with that in Example 1. The obtained catalyst was used in Example 181, and the composition is listed in Table 26.

Example 73

Catalyst containing lithium carbonate ($Li_2CO_3$) 1.20 g instead of sodium carbonate 2.24 g was prepared by the same procedure with that in Example 1. The obtained catalyst was used in Example 182, and the composition is listed in Table 26.

Example 74

Catalyst containing rubidium carbonate ($Rb_2CO_3$) 0.60 g instead of sodium carbonate 2.24 g was prepared by the same procedure with that in Example 1. The obtained catalyst was used in Example 183, and the composition is listed in Table 26.

Example 75

Catalyst containing cesium carbonate ($Cs_2CO_3$) 0.56 g instead of sodium carbonate 2.24 g was prepared by the same procedure with that in Example 1. The obtained catalyst was used in Example 184, and the composition is listed in Table 26.

Example 76

Iron nitrate ($Fe(NO_3)_3.9H_2O$) 200 g and nickel nitrate ($Ni(NO_3)_2.6H_2O$) 144 g were dissolved to ion exchanged water 500 ml. Sodium hydroxide of approximately 100 g was dissolved to ion exchanged water 500 ml. Both solutions were added dropwise to an ion exchanged water 2 liter at room temperature while maintaining the pH in a range of from 7 to 8. After completing the dropwise addition, the solution was agitated for approximately 1 hr. The generated precipitate was filtered and washed.

The obtained gel was mixed with aqueous solution 100 ml containing sodium carbonate ($Na_2CO_3.10H_2O$) 3.70 g, and with aqueous solution 25 ml prepared by dissolving ammonium methavanadate ($NH_4VO_3$) 2.06 g and oxalic acid ($(COOH)_2$) 4 g, and with aqueous solution 25 ml prepared by dissolving ammonium molybdate $(NH_4)_6Mo_7O_{24}.4H_2O$) 1.47 g. The mixture was agitated for approximately 1 hr. to obtain a gel. The gel was dried in air at 120° C. for 24 hrs., followed by calcining in air at 800° C. for 4 hrs. to obtain the catalyst.

The catalyst had the composition of $Fe_2O_3:NiO:Na_2O:V_2O_5:MoO_3$=49.3:46.2:1.0:2.0:1.5 (by weight).

Example 77

Iron nitrate ($Fe(NO_3)_3.9H_2O$) 200 g and nickel nitrate ($Ni(NO_3)_2.6H_2O$) 144 g were dissolved to ion exchanged water 500 ml. Sodium hydroxide of approximately 100 g was dissolved to ion exchanged water 500 ml. Both solutions were added dropwise to an ion exchanged water 2 liter at room temperature while maintaining the pH in a range of from 7 to 8. After completing the dropwise addition, the solution was agitated for approximately 1 hr. The generated precipitate was filtered and washed.

The obtained gel was mixed with aqueous solution 100 ml containing sodium carbonate ($Na_2CO_3.10H_2O$) 3.70 g. The mixture was agitated for approximately 1 hr. The gel was dried in air at 120° C. for 24 hrs., followed by calcining in air at 800° C. for 4 hrs.

The calcined product was powdered, and was mixed with a vanadium pentoxide powder ($V_2O_5$) 1.55 g. The mixture was compressed to form into cylindrical catalyst having the radius of 1 mm and the length of 5 mm.

The catalyst had the composition of $Fe_2O_3$:NiO:$Na_2O$:$V_2O_5$=50.3:47.1:0.6:2.0 (by weight).

Example 78

Iron nitrate ($Fe(NO_3)_3.9H_2O$) 200 g and nickel nitrate ($Ni(NO_3)_2.6H_2O$) 144 g were dissolved to ion exchanged water 500 ml. Sodium hydroxide of approximately 100 g was dissolved to ion exchanged water 500 ml. Both solutions were added dropwise to an ion exchanged water 2 liter at room temperature while maintaining the pH in a range of from 7 to 8. After completing the dropwise addition, the solution was agitated for approximately 1 hr. The generated precipitate was filtered and washed.

The obtained gel was dried in air at 120° C. for 24 hrs., followed by calcining in air at 800° C. for 4 hrs.

The fired product was put into an aqueous solution 100 ml containing sodium carbonate ($Na_2CO_3.10H_2O$) 2.24 g. and an aqueous solution 50 ml prepared by dissolving ammonium methavanadate ($NH_4VO_3$) 2 g and oxalic acid ($(COOH)_2$) 4 g. The mixture was evaporated to dry, followed by drying at 120° C. for 24 hrs. and calcining at 500° C. for 3 hrs. to obtain the catalyst. The catalyst had the composition of $Fe_2O_3$:NiO:$Na_2O$:$V_2O_5$=50.3:47.1:0.6:2.0 (by weight).

Example 79

Powders of hydroxyl-iron oxide (FeO(OH)) 43.98 g, nickel hydroxide ($Ni(OH)_2$) 45.9 g, sodium carbonate ($Na_2CO_3.10H_2O$) 3.70 g, and vanadium pentoxide ($V_2O_5$) 1.55 g were mixed together. The mixture was calcined in air at 800° C. for 4 hrs. The calcined product was compressed to form into cylindrical catalyst having the radius of 1 mm and the length of 5 mm. The catalyst had the composition of $Fe_2O_3$:NiO:$Na_2O$:$V_2O_5$=50.3:47.1:0.6:2.0 (by weight).

Example 80

Catalyst containing magnesium nitrate ($Mg(NO_3)_2.6H_2O$) 3.09 g instead of sodium carbonate 2.24 g was prepared by the same procedure with that in Example 1. The obtained catalyst was used in Example 189, and the composition is listed in Table 28.

Example 81

Catalyst containing calcium nitrate ($Ca(NO_3)_2.4H_2O$) 2.04 g instead of sodium carbonate 2.24 g was prepared by the same procedure with that in Example 1. The obtained catalyst was used in Example 190, and the composition is listed in Table 28.

Example 82

Catalyst containing strontium nitrate ($Sr(NO_3)_2$) 0.99 g instead of sodium carbonate 2.24 g was prepared by the same procedure with that in Example 1. The obtained catalyst was used in Example 191, and the composition is listed in Table 28.

Example 83

Catalyst containing barium nitrate($Ba(NO_3)_2$) 0.83 g instead of sodium carbonate 2.24 g was prepared by the same procedure with that in Example 1. The obtained catalyst was used in Example 192, and the composition is listed in Table 28.

Example 84

Catalyst containing magnesium nitrate ($Mg(NO_3)_2.6H_2O$) 5.08 g instead of sodium carbonate 3.68 g was prepared by the same procedure with that in Example 32. The obtained catalyst was used in Example 193, and the composition is listed in Table 29.

Example 85

Catalyst containing calcium nitrate ($Ca(NO_3)_2.4H_2O$) 3.35 g instead of sodium carbonate 3.68 g was prepared by the same procedure with that in Example 32. The obtained catalyst was used in Example 194, and the composition is listed in Table 29.

Example 86

Catalyst containing barium nitrate ($Ba(NO_3)_2$) 1.36 g instead of sodium carbonate 3.68 g was prepared by the same procedure with that in Example 32. The obtained catalyst was used in Example 195, and the composition is listed in Table 29.

Comparative Example 1

A catalyst was prepared by the same procedure with that in Example 1 except for not using ammonium methavanadate and oxalic acid.

Comparative Example 2

A catalyst was prepared in accordance with the Example 1 described in JP-B-64-934. A γ-alumina 30 g was dipped into a solution of ion exchanged water 80 g containing ammonium molybdate 1.73 g, ammonium methavanadate 1.72 g, copper nitrate 4.14 g, 28% aqueous ammonia 75 g, and monoethanol amine 4 g. After heating the mixture at 80° C. for 10 min., the mixture was evaporated to dry in an evaporator under a reduced pressure for 1 hr., followed by calcining at 750° C. for 3 hrs. The obtained catalyst was dipped into an ion exchanged water 20 g containing sodium hydroxide 2.74 g. Then the catalyst was evaporated to dry in an evaporator, followed by calcining at 600° C. for 8 hrs.

Comparative Example 3

A catalyst was prepared in accordance with the Example 1 described in JP-B-59-20384. Copper sulfate 120 g and zirconium oxynitrate 18 g were dissolved to ion exchanged water 30 g. The mixture was heated to 70 to 80° C. An α-alumina 100 g was dipped into the solution. The solution was dried, and calcined at 750° C. for 2 hrs. The catalyst was dipped into an ion exchanged water 30 g containing potassium hydroxide 4.3 g, followed by drying and by calcining at 500° C. for 16 hrs.

II. Reaction Method

Each catalyst was pulverized to a specified size, which was then filled into a quartz tube having an inside diameter of 20 mm. to a specified quantity. A predetermined amount of benzoic acid, steam, and air were introduced to the tube to react them at a specified temperature.

III. Condition and Result of Reaction

Examples 87–90

The catalyst of Example 1 was used under various reaction temperature levels. The condition and result of the reaction are summarized in Table 1.

Examples 91–98

The catalyst of Example 1 was used under various Space Velocity. The condition and result of the reaction are summarized in Tables 2 and 3.

Examples 99–102

The catalyst of Example 1 was used under various air concentrations. The condition and result of the reaction are summarized in Table 4.

Examples 103–106

The catalyst of Example 1 was used under various steam quantities. The condition and result of the reaction are summarized in Table 5.

Examples 107–110

The catalyst of Example 1 was used under various raw materials. The condition and result of the reaction are summarized in Table 6.

Examples 111–114

Catalysts of Examples 2 through 5 were used. The condition and result of reaction are summarized in Table 7.

Examples 115–117

Catalysts of Examples 6 through 8 were used. The condition and result of reaction are summarized in Table 8.

Examples 118–121

Catalysts of Examples 9 through 12 were used. The condition and result of reaction are summarized in Table 9.

Examples 122–124

Catalysts of Examples 13 through 15 were used. The condition and result of reaction are summarized in Table 10.

Examples 125–129

Catalysts of Examples 16 through 20 were used. The condition and result of reaction are summarized in Table 11.

Examples 130–133

Catalysts of Examples 21 through 24 were used. The condition and result of reaction are summarized in Table 12.

Examples 134–135

Catalysts of Examples 25 and 26 were used. The condition and result of reaction are summarized in Table 13.

Examples 136–140

Catalysts of Examples 27 through 31 were used. The condition and result of reaction are summarized in Table 14.

Examples 141–144

Catalysts of Examples 32 through 35 were used. The condition and result of reaction are summarized in Table 15.

Examples 145–147

Catalysts of Examples 36 through 38 were used. The condition and result of reaction are summarized in Table 16.

Examples 148–151

Catalysts of Examples 39 through 42 were used. The condition and result of reaction are summarized in Table 17.

Examples 152–154

Catalysts of Examples 43 through 45 were used. The condition and result of reaction are summarized in Table 18.

Examples 155–159

Catalysts of Examples 46 through 50 were used. The condition and result of reaction are summarized in Table 19.

Examples 160–163

Catalysts of Examples 51 through 54 were used. The condition and result of reaction are summarized in Table 20.

Examples 164–165

Catalysts of Examples 55 and 56 were used. The condition and result of reaction are summarized in Table 21.

Examples 166–170

Catalysts of Examples 57 through 61 were used. The condition and result of reaction are summarized in Table 22.

Examples 171–174

Catalysts of Examples 62 through 65 were used. The condition and result of reaction are summarized in Table 23.

Examples 175–178

Catalysts of Examples 66 through 69 were used. The condition and result of reaction are summarized in Table 24.

Examples 179–180

Catalysts of Examples 70 and 71 were used. The condition and result of reaction are summarized in Table 25.

Examples 181–184

Catalysts of Examples 72 through 75 were used. The condition and result of reaction are summarized in Table 26.

Examples 185–188

Catalysts of Examples 76 through 79 were used. The condition and result of reaction are summarized in Table 27.

Examples 189–192

Catalysts of Examples 80 through 83 were used. The condition and result of reaction are summarized in Table 28.

Examples 193–195

Catalysts of Examples 84 through 86 were used with o-toluic acid as the raw material. The condition and result of reaction are summarized in Table 29.

Comparative Examples 4–6

Catalysts of Comparative Examples 1 through 3 were used. The condition and result of reaction are summarized in Table 30.

Example 196 and Comparative Examples 7 and 8

Catalysts of Example 62, Comparative Examples 2 and 3 were used with o-toluic acid as the raw material. The condition and result of reaction are summarized in Table 31.

TABLE 1

| | | | Example 87 | Example 88 |
|---|---|---|---|---|
| Catalyst | Composition (wt. ratio) | | $Fe_2O_3$—NiO—$Na_2O$—$V_2O_5$ (50.3:47.1:0.6:2.0) | $Fe_2O_3$—NiO—$Na_2O$—$V_2O_5$ (50.3:47.1:0.6:2.0) |
| | Calcining temperature (° C.)* | | 800 | 800 |
| | Use quantity (ml) | | 5.5 | 5.5 |
| Reaction condition | Reaction Temperature (° C.) | | 420 | 400 |
| | Feed gas concentration (%) | Benzoic acid | 3.8 | 3.8 |
| | | Water vapor | 76.9 | 76.9 |
| | | Oxygen | 3.8 | 3.8 |
| | | Nitrogen | 15.4 | 15.4 |
| | Space velocity ($h^{-1}$) | | 2150 | 3400 |
| | Time after the start of reaction (h) | | 110 | 110 |
| Reaction result | Conversion of benzoic acid (%) | | 93.7 | 90.5 |
| | Selectivity** | Phenol | 91.0 | 90.9 |
| | | Benzene | 4.7 | 8.1 |
| | | CO, $CO_2$ | 4.3 | 0.8 |
| | Space time yield of phenol (g/l · h) | | 292 | 446 |

| | | | Example 89 | Example 90 |
|---|---|---|---|---|
| Catalyst | Composition (wt. ratio) | | $Fe_2O_3$—NiO—$Na_2O$—$V_2O_5$ (50.3:47.1:0.6:2.0) | $Fe_2O_3$—NiO—$Na_2O$—$V_2O_5$ (50.3:47.1:0.6:2.0) |
| | Calcining temperature (° C.)* | | 800 | 800 |
| | Use quantity (ml) | | 5.5 | 5.5 |
| Reaction condition | Reaction Temperature (° C.) | | 300 | 500 |
| | Feed gas concentration (%) | Benzoic acid | 3.8 | 3.8 |
| | | Water vapor | 76.9 | 76.9 |
| | | Oxygen | 3.8 | 3.8 |
| | | Nitrogen | 15.4 | 15.4 |
| | Space velocity ($h^{-1}$) | | 3400 | 3400 |
| | Time after the start of reaction (h) | | 110 | 110 |
| Reaction result | Conversion of benzoic acid (%) | | 27.5 | 100.0 |
| | Selectivity** | Phenol | 95.9 | 84.3 |
| | | Benzene | 3.6 | 15.2 |
| | | CO, $CO_2$ | 0.3 | 0.4 |
| | Space time yield of phenol (g/l · h) | | 143 | 457 |

*Calcining temperature of $Fe_2O_3$—NiO—$Na_2O$ before supporting $V_2O_5$.
**C-mol %

TABLE 2

| | | | Example 91 | Example 92 |
|---|---|---|---|---|
| Catalyst | Composition (wt. ratio) | | $Fe_2O_3$—NiO—$Na_2O$—$V_2O_5$ (50.3:47.1:0.6:2.0) | $Fe_2O_3$—NiO—$Na_2O$—$V_2O_5$ (50.3:47.1:0.6:2.0) |
| | Calcining temperature (° C.)* | | 800 | 800 |
| | Use quantity (ml) | | 5.5 | 5.5 |
| Reaction condition | Reaction Temperature (° C.) | | 420 | 420 |
| | Feed gas concentration (%) | Benzoic acid | 3.8 | 3.8 |
| | | Water vapor | 76.9 | 76.9 |
| | | Oxygen | 3.8 | 3.8 |
| | | Nitrogen | 15.4 | 15.4 |
| | Space velocity ($h^{-1}$) | | 1250 | 3800 |
| | Time after the start of reaction (h) | | 110 | 110 |
| Reaction result | Conversion of benzoic acid (%) | | 100.0 | 90.0 |
| | Selectivity** | Phenol | 94.0 | 90.1 |
| | | Benzene | 2.5 | 8.4 |
| | | CO, $CO_2$ | 3.3 | 0.8 |
| | Space time yield of phenol (g/l · h) | | 187 | 496 |

TABLE 2-continued

| | | | Example 93 | Example 94 |
|---|---|---|---|---|
| Catalyst | Composition (wt. ratio) | | $Fe_2O_3$—NiO—$Na_2O$—$V_2O_5$ (50.3:47.1:0.6:2.0) | $Fe_2O_3$—NiO—$Na_2O$—$V_2O_5$ (50.3:47.1:0.6:2.0) |
| | Calcining temperature (° C.)* | | 800 | 800 |
| | Use quantity (ml) | | 5.5 | 5.5 |
| Reaction condition | Reaction Temperature (° C.) | | 420 | 420 |
| | Feed gas concentration (%) | Benzoic acid | 3.8 | 3.8 |
| | | Water vapor | 76.9 | 76.9 |
| | | Oxygen | 3.8 | 3.8 |
| | | Nitrogen | 15.4 | 15.4 |
| | Space velocity ($h^{-1}$) | | 5500 | 8020 |
| | Time after the start of reaction (h) | | 110 | 110 |
| Reaction result | Conversion of benzoic acid (%) | | 87.5 | 85.0 |
| | Selectivity** | Phenol | 91.9 | 90.3 |
| | | Benzene | 7.6 | 8.2 |
| | | CO, $CO_2$ | 0.2 | 1.4 |
| | Space time yield of phenol (g/l · h) | | 705 | 982 |

*Calcining temperature of $Fe_2O_3$—NiO—$Na_2O$ before supporting $V_2O_5$.
**C-mol %

TABLE 3

| | | | Example 95 | Example 96 |
|---|---|---|---|---|
| Catalyst | Composition (wt. ratio) | | $Fe_2O_3$—NiO—$Na_2O$—$V_2O_5$ (50.3:47.1:0.6:2.0) | $Fe_2O_3$—NiO—$Na_2O$—$V_2O_5$ (50.3:47.1:0.6:2.0) |
| | Calcining temperature (° C.)* | | 800 | 800 |
| | Use quantity (ml) | | 5.5 | 5.5 |
| Reaction condition | Reaction Temperature (° C.) | | 420 | 420 |
| | Feed gas concentration (%) | Benzoic acid | 3.8 | 3.8 |
| | | Water vapor | 76.9 | 76.9 |
| | | Oxygen | 3.8 | 3.8 |
| | | Nitrogen | 15.4 | 15.4 |
| | Space velocity ($h^{-1}$) | | 9500 | 15000 |
| | Time after the start of reaction (h) | | 110 | 110 |
| Reaction result | Conversion of benzoic acid (%) | | 76.9 | 50.6 |
| | Selectivity** | Phenol | 91.0 | 90.4 |
| | | Benzene | 5.7 | 7.2 |
| | | CO, $CO_2$ | 3.3 | 1.8 |
| | Space time yield of phenol (g/l · h) | | 1060 | 1094 |

| | | | Example 97 | Example 98 |
|---|---|---|---|---|
| Catalyst | Composition (wt. ratio) | | $Fe_2O_3$—NiO—$Na_2O$—$V_2O_5$ (50.3:47.1:0.6:2.0) | $Fe_2O_3$—NiO—$Na_2O$—$V_2O_5$ (50.3:47.1:0.6:2.0) |
| | Calcining temperature (° C.)* | | 800 | 800 |
| | Use quantity (ml) | | 5.5 | 5.5 |
| Reaction condition | Reaction Temperature (° C.) | | 420 | 420 |
| | Feed gas concentration (%) | Benzoic acid | 3.8 | 3.8 |
| | | Water vapor | 76.9 | 76.9 |
| | | Oxygen | 3.8 | 3.8 |
| | | Nitrogen | 15.4 | 15.4 |
| | Space velocity ($h^{-1}$) | | 18000 | 21000 |
| | Time after the start of reaction (h) | | 110 | 110 |
| Reaction result | Conversion of benzoic acid (%) | | 47.3 | 27.4 |
| | Selectivity** | Phenol | 90.5 | 92.3 |
| | | Benzene | 8.5 | 7.2 |
| | | CO, $CO_2$ | 0.3 | 0.5 |
| | Space time yield of phenol (g/l · h) | | 1229 | 847 |

*Calcining temperature of $Fe_2O_3$—NiO—$Na_2O$ before supporting $V_2O_5$.
**C-mol %

TABLE 4

| | | | Example 99 | Example 100 |
|---|---|---|---|---|
| Catalyst | Composition (wt. ratio) | | $Fe_2O_3$—NiO—$Na_2O$—$V_2O_5$ (50.3:47.1:0.6:2.0) | $Fe_2O_3$—NiO—$Na_2O$—$V_2O_5$ (50.3:47.1:0.6:2.0) |
| | Calcining temperature (° C.)* | | 800 | 800 |
| | Use quantity (ml) | | 5.5 | 5.5 |
| Reaction condition | Reaction Temperature (° C.) | | 420 | 420 |
| | Feed gas concentration (%) | Benzoic acid | 3.8 | 3.8 |
| | | Water vapor | 76.9 | 76.9 |
| | | Oxygen | 1.9 | 7.6 |
| | | Nitrogen | 17.3 | 11.6 |
| | Space velocity ($h^{-1}$) | | 3400 | 3400 |
| | Time after the start of reaction (h) | | 110 | 110 |
| Reaction result | Conversion of benzoic acid (%) | | 69.7 | 99.8 |
| | Selectivity** | Phenol | 92.0 | 85.3 |
| | | Benzene | 3.7 | 10.1 |
| | | CO, $CO_2$ | 3.3 | 4.5 |
| | Space time yield of phenol (g/l · h) | | 348 | 461 |

| | | | Example 101 | Example 102 |
|---|---|---|---|---|
| Catalyst | Composition (wt. ratio) | | $Fe_2O_3$—NiO—$Na_2O$—$V_2O_5$ (50.3:47.1:0.6:2.0) | $Fe_2O_3$—NiO—$Na_2O$—$V_2O_5$ (50.3:47.1:0.6:2.0) |
| | Calcining temperature (° C.)* | | 800 | 800 |
| | Use quantity (ml) | | 5.5 | 5.5 |
| Reaction condition | Reaction Temperature (° C.) | | 420 | 420 |
| | Feed gas concentration (%) | Benzoic acid | 3.8 | 0.6 |
| | | Water vapor | 76.9 | 11.7 |
| | | Oxygen | 15.4 | 17.5 |
| | | Nitrogen | 3.8 | 70.2 |
| | Space velocity ($h^{-1}$) | | 3400 | 3400 |
| | Time after the start of reaction (h) | | 110 | 110 |
| Reaction result | Conversion of benzoic acid (%) | | 100.0 | 100.0 |
| | Selectivity** | Phenol | 85.9 | 80.2 |
| | | Benzene | 10.6 | 16.2 |
| | | CO, $CO_2$ | 3.5 | 3.6 |
| | Space time yield of phenol (g/l · h) | | 466 | 69 |

*Calcining temperature of $Fe_2O_3$—NiO—$Na_2O$ before supporting $V_2O_5$.
**C-mol %

TABLE 5

| | | | Example 103 | Example 104 |
|---|---|---|---|---|
| Catalyst | Composition (wt. ratio) | | $Fe_2O_3$—NiO—$Na_2O$—$V_2O_5$ (50.3:47.1:0.6:2.0) | $Fe_2O_3$—NiO—$Na_2O$—$V_2O_5$ (50.3:47.1:0.6:2.0) |
| | Calcining temperature (° C.)* | | 800 | 800 |
| | Use quantity (ml) | | 5.5 | 5.5 |
| Reaction condition | Reaction Temperature (° C.) | | 420 | 420 |
| | Feed gas concentration (%) | Benzoic acid | 9.1 | 6.3 |
| | | Water vapor | 45.5 | 62.5 |
| | | Oxygen | 9.1 | 6.3 |
| | | Nitrogen | 36.3 | 24.9 |
| | Space velocity ($h^{-1}$) | | 1440 | 2090 |
| | Time after the start of reaction (h) | | 110 | 110 |
| Reaction result | Conversion of benzoic acid (%) | | 90.5 | 92.8 |
| | Selectivity** | Phenol | 85.8 | 88.4 |
| | | Benzene | 8.7 | 7.1 |
| | | CO, $CO_2$ | 3.2 | 2.5 |
| | Space time yield of phenol (g/l · h) | | 427 | 453 |

| | | | Example 105 | Example 106 |
|---|---|---|---|---|
| Catalyst | Composition (wt. ratio) | | $Fe_2O_3$—NiO—$Na_2O$—$V_2O_5$ (50.3:47.1:0.6:2.0) | $Fe_2O_3$—NiO—$Na_2O$—$V_2O_5$ (50.3:47.1:0.6:2.0) |
| | Calcining temperature (° C.)* | | 800 | 800 |
| | Use quantity (ml) | | 5.5 | 5.5 |

TABLE 5-continued

| | | | | |
|---|---|---|---|---|
| Reaction condition | Reaction Temperature (° C.) | | 420 | 420 |
| | Feed gas concentration (%) | Benzoic acid | 2.8 | 1.8 |
| | | Water vapor | 83.3 | 89.3 |
| | | Oxygen | 2.8 | 1.8 |
| | | Nitrogen | 11.1 | 7.1 |
| | Space velocity ($h^{-1}$) | | 4710 | 7320 |
| Time after the start of reaction (h) | | | 110 | 110 |
| Reaction result | Conversion of benzoic acid (%) | | 95.0 | 95.2 |
| | Selectivity** | Phenol | 93.1 | 93.0 |
| | | Benzene | 3.2 | 3.4 |
| | | CO, $CO_2$ | 3.5 | 3.6 |
| | Space time yield of phenol (g/l · h) | | 489 | 490 |

*Calcining temperature of $Fe_2O_3$—NiO—$Na_2O$ before supporting $V_2O_5$.
**C-mol %

TABLE 6

| | | | Example 107 | Example 108 |
|---|---|---|---|---|
| Catalyst | Composition (wt. ratio) | | $Fe_2O_3$—NiO—$Na_2O$—$V_2O_5$ (50.3:47.1:0.6:2.0) | $Fe_2O_3$—NiO—$Na_2O$—$V_2O_5$ (50.3:47.1:0.6:2.0) |
| | Calcining temperature (° C.)* | | 800 | 800 |
| | Use quantity (ml) | | 5.5 | 5.5 |
| Reaction condition | Alkyl benzoic acid group as raw material | | o-toluic acid | p-toluic acid |
| | Reaction Temperature (° C.) | | 420 | 420 |
| | Feed gas concentration (%) | Alkyl benzoic acid | 3.8 | 3.8 |
| | | Water vapor | 76.9 | 76.9 |
| | | Oxygen | 3.8 | 3.8 |
| | | Nitrogen | 15.4 | 15.4 |
| | Space velocity ($h^{-1}$) | | 3400 | 3400 |
| Time after the start of reaction (h) | | | 110 | 110 |
| Reaction result | Conversion of raw material (%) | | 35.6 | 56.2 |
| | Selectivity** | Alkyl phenol group | 65.8 (m-cresol) | 78.4 (m-cresol) |
| | | CO, $CO_2$ | 11.2 | 12.2 |
| | Space time yield of phenol (g/l · h) | | 146 | 275 |

| | | | Example 109 | Example 110 |
|---|---|---|---|---|
| Catalyst | Composition (wt. ratio) | | $Fe_2O_3$—NiO—$Na_2O$—$V_2O_5$ (50.3:47.1:0.6:2.0) | $Fe_2O_3$—NiO—$Na_2O$—$V_2O_5$ (50.3:47.1:0.6:2.0) |
| | Calcining temperature (° C.)* | | 800 | 800 |
| | Use quantity (ml) | | 5.5 | 5.5 |
| Reaction condition | Alkyl benzoic acid group as raw material | | p-isopropyl benzoic acid | p-ethyl benzoic acid |
| | Reaction Temperature (° C.) | | 420 | 420 |
| | Feed gas concentration (%) | Alkyl benzoic acid | 3.8 | 3.8 |
| | | Water vapor | 76.9 | 76.9 |
| | | Oxygen | 3.8 | 3.8 |
| | | Nitrogen | 15.4 | 15.4 |
| | Space velocity ($h^{-1}$) | | 3400 | 3400 |
| Time after the start of reaction (h) | | | 110 | 110 |
| Reaction result | Conversion of raw material (%) | | 25.9 | 33.2 |
| | Selectivity** | Alkyl phenol group | 53.1 (m-isopropyl phenol) | 33.0 (m-ethyl phenol) |
| | | CO, $CO_2$ | 22.1 | 24.1 |
| | Space time yield of phenol (g/l · h) | | 108 | 77 |

*Calcining temperature of $Fe_2O_3$—NiO—$Na_2O$ before supporting $V_2O_5$.
**C-mol %

TABLE 7

| | | | Example 111 | Example 112 |
|---|---|---|---|---|
| Catalyst | Composition (wt. ratio) | | $Fe_2O_3$—NiO—$Na_2O$—$V_2O_5$ (49.8:46.7:0.6:3.0) | $Fe_2O_3$—NiO—$Na_2O$—$V_2O_5$ (49.2:44.8:0.6:4.0) |
| | Calcining temperature (° C.)* | | 800 | 800 |
| | Use quantity (ml) | | 6.5 | 6.5 |
| Reaction condition | Reaction Temperature (° C.) | | 410 | 410 |
| | Feed gas concentration (%) | Benzoic acid | 3.2 | 3.2 |
| | | Water vapor | 80.6 | 80.6 |
| | | Oxygen | 3.2 | 3.2 |
| | | Nitrogen | 12.9 | 12.9 |
| | Space velocity ($h^{-1}$) | | 3400 | 3400 |
| Time after the start of reaction (h) | | | 95 | 92 |
| Reaction result | Conversion of benzoic acid (%) | | 90.6 | 87.5 |
| | Selectivity** | Phenol | 90.8 | 90.9 |
| | | Benzene | 8.2 | 8.6 |
| | | CO, $CO_2$ | 0.8 | 0.3 |
| | Space time yield of phenol (g/l · h) | | 376 | 363 |

| | | | Example 113 | Example 114 |
|---|---|---|---|---|
| Catalyst | Composition (wt. ratio) | | $Fe_2O_3$—NiO—$Na_2O$—$V_2O_5$ (47.7:44.7:0.6:7.0) | $Fe_2O_3$—NiO—$Na_2O$—$V_2O_5$ (46.1:43.3:0.6:10.0) |
| | Calcining temperature (° C.)* | | 800 | 800 |
| | Use quantity (ml) | | 6.5 | 5.5 |
| Reaction condition | Reaction Temperature (° C.) | | 410 | 420 |
| | Feed gas concentration (%) | Benzoic acid | 3.1 | 3.8 |
| | | Water vapor | 78.1 | 76.9 |
| | | Oxygen | 3.1 | 3.8 |
| | | Nitrogen | 12.5 | 15.4 |
| | Space velocity ($h^{-1}$) | | 3400 | 3400 |
| Time after the start of reaction (h) | | | 104 | 110 |
| Reaction result | Conversion of benzoic acid (%) | | 87.1 | 83.7 |
| | Selectivity** | Phenol | 93.3 | 88.0 |
| | | Benzene | 6.2 | 6.7 |
| | | CO, $CO_2$ | 0.5 | 4.3 |
| | Space time yield of phenol (g/l · h) | | 359 | 399 |

*Calcining temperature of $Fe_2O_3$—NiO—$Na_2O$ before supporting $V_2O_5$.
**C-mol %

TABLE 8

| | | | Example 115 | Example 116 | Example 117 |
|---|---|---|---|---|---|
| Catalyst | Composition (wt. ratio) | | $Fe_2O_3$—NiO—$Na_2O$—$V_2O_5$ (49.8:46.7:0.6:1.0) | $Fe_2O_3$—NiO—$Na_2O$—$V_2O_5$ (49.2:44.8:0.6:0.5) | $Fe_2O_3$—NiO—$Na_2O$—$V_2O_5$ (47.7:44.7:0.6:0.1) |
| | Calcining temperature (° C.)* | | 800 | 800 | 800 |
| | Use quantity (ml) | | 6.5 | 6.5 | 6.5 |
| Reaction condition | Reaction Temperature (° C.) | | 410 | 410 | 410 |
| | Feed gas concentration (%) | Benzoic acid | 3.8 | 3.8 | 3.8 |
| | | Water vapor | 76.9 | 76.9 | 76.9 |
| | | Oxygen | 3.8 | 3.8 | 3.8 |
| | | Nitrogen | 15.4 | 15.4 | 15.4 |
| | Space velocity ($h^{-1}$) | | 3400 | 3400 | 3400 |
| Time after the start of reaction (h) | | | 110 | 110 | 110 |
| Reaction result | Conversion of benzoic acid (%) | | 90.5 | 87.5 | 67.3 |
| | Selectivity** | Phenol | 88.8 | 81.2 | 80.3 |
| | | Benzene | 10.2 | 14.6 | 15.2 |
| | | CO, $CO_2$ | 0.8 | 3.3 | 4.5 |
| | Space time yield of phenol (g/l · h) | | 436 | 385 | 293 |

*Calcining temperature of $Fe_2O_3$—NiO—$Na_2O$ before supporting $V_2O_5$.
**C-mol %

TABLE 9

| | | | Example 118 | Example 119 |
|---|---|---|---|---|
| Catalyst | Composition (wt. ratio) | | $Fe_2O_3$—NiO—$Na_2O$—$V_2O_5$ (50.5:47.4:0.05:2.0) | $Fe_2O_3$—NiO—$Na_2O$—$V_2O_5$ (50.5:47.3:0.2:2.0) |
| | Calcining temperature (° C.)* | | 800 | 800 |
| | Use quantity (ml) | | 5.5 | 5.5 |
| Reaction condition | Reaction Temperature (° C.) | | 420 | 400 |
| | Feed gas concentration (%) | Benzoic acid | 3.8 | 3.8 |
| | | Water vapor | 76.9 | 76.9 |
| | | Oxygen | 3.8 | 3.8 |
| | | Nitrogen | 15.4 | 15.4 |
| | Space velocity ($h^{-1}$) | | 3400 | 3400 |
| Time after the start of reaction (h) | | | 110 | 110 |
| Reaction result | Conversion of benzoic acid (%) | | 59.6 | 63.3 |
| | Selectivity** | Phenol | 90.0 | 90.8 |
| | | Benzene | 6.3 | 7.2 |
| | | CO, $CO_2$ | 2.9 | 1.8 |
| | Space time yield of phenol (g/l · h) | | 291 | 312 |

| | | | Example 120 | Example 121 |
|---|---|---|---|---|
| Catalyst | Composition (wt. ratio) | | $Fe_2O_3$—NiO—$Na_2O$—$V_2O_5$ (50.1:46.9:1.0:2.0) | $Fe_2O_3$—NiO—$Na_2O$—$V_2O_5$ (46.5:46.5:2.0:2.0) |
| | Calcining temperature (° C.)* | | 800 | 800 |
| | Use quantity (ml) | | 5.5 | 5.5 |
| Reaction condition | Reaction Temperature (° C.) | | 300 | 500 |
| | Feed gas concentration (%) | Benzoic acid | 3.8 | 3.8 |
| | | Water vapor | 76.9 | 76.9 |
| | | Oxygen | 3.8 | 3.8 |
| | | Nitrogen | 15.4 | 15.4 |
| | Space velocity ($h^{-1}$) | | 3400 | 3400 |
| Time after the start of reaction (h) | | | 110 | 110 |
| Reaction result | Conversion of benzoic acid (%) | | 90.2 | 94.4 |
| | Selectivity** | Phenol | 92.3 | 91.0 |
| | | Benzene | 5.4 | 5.3 |
| | | CO, $CO_2$ | 2.3 | 2.9 |
| | Space time yield of phenol (g/l · h) | | 451 | 466 |

*Calcining temperature of $Fe_2O_3$—NiO—$Na_2O$ before supporting $V_2O_5$.
**C-mol %

TABLE 10

| | | | Example 122 | Example 123 | Example 124 |
|---|---|---|---|---|---|
| Catalyst | Composition (wt. ratio) | | $Fe_2O_3$—NiO—$Na_2O$—$V_2O_5$ (48.0:45.0:5.0:2.0) | $Fe_2O_3$—NiO—$Na_2O$—$V_2O_5$ (45.4:41.1:10.0:2.0) | $Fe_2O_3$—NiO—$Na_2O$—$V_2O_5$ (35.1:32.9:30.0:2.0) |
| | Calcining temperature (° C.)* | | 800 | 800 | 800 |
| | Use quantity (ml) | | 5.5 | 5.5 | 5.5 |
| Reaction condition | Reaction Temperature (° C.) | | 420 | 400 | 300 |
| | Feed gas concentration (%) | Benzoic acid | 3.8 | 3.8 | 3.8 |
| | | Water vapor | 76.9 | 76.9 | 76.9 |
| | | Oxygen | 3.8 | 3.8 | 3.8 |
| | | Nitrogen | 15.4 | 15.4 | 15.4 |
| | Space velocity ($h^{-1}$) | | 2150 | 3400 | 3400 |
| Time after the start of reaction (h) | | | 110 | 110 | 110 |
| Reaction result | Conversion of benzoic acid (%) | | 93.4 | 66.3 | 47.5 |
| | Selectivity** | Phenol | 90.1 | 77.9 | 64.9 |
| | | Benzene | 5.7 | 18.4 | 22.3 |
| | | CO, $CO_2$ | 3.9 | 2.9 | 12.2 |
| | Space time yield of phenol (g/l · h) | | 456 | 280 | 167 |

*Calcining temperature of $Fe_2O_3$—NiO—$Na_2O$ before supporting $V_2O_5$.
**C-mol %

TABLE 11

| | | | Example 125 | Example 126 | Example 127 |
|---|---|---|---|---|---|
| Catalyst | Composition (wt. ratio) | | $Fe_2O_3$—NiO—$Na_2O$—$V_2O_5$ (50.0:46.9:1.0:3.0) | $Fe_2O_3$—NiO—$Na_2O$—$V_2O_5$ (47.5:44.5:2.0:6.0) | $Fe_2O_3$—NiO—$Na_2O$—$V_2O_5$ (45.4:42.6:3.0:9.0) |
| | Calcining temperature (° C.)* | | 800 | 800 | 800 |
| | Use quantity (ml) | | 6.5 | 6.5 | 6.5 |
| Reaction condition | Reaction Temperature (° C.) | | 410 | 410 | 410 |
| | Feed gas concentration (%) | Benzoic acid | 3.1 | 3.1 | 3.2 |
| | | Water vapor | 78.1 | 78.1 | 80.6 |
| | | Oxygen | 3.1 | 3.1 | 3.2 |
| | | Nitrogen | 12.5 | 12.5 | 12.9 |
| | Space velocity ($h^{-1}$) | | 3400 | 3400 | 3400 |
| Time after the start of reaction (h) | | | 104 | 101 | 93 |
| Reaction result | Conversion of benzoic acid (%) | | 87.1 | 88.4 | 53.8 |
| | Selectivity** | Phenol | 93.3 | 92.1 | 88.0 |
| | | Benzene | 6.2 | 6.6 | 8.1 |
| | | CO, $CO_2$ | 0.5 | 1.1 | 3.8 |
| | Space time yield of phenol (g/l · h) | | 359 | 360 | 216 |

| | | | Example 128 | Example 129 |
|---|---|---|---|---|
| Catalyst | Composition (wt. ratio) | | $Fe_2O_3$—NiO—$Na_2O$—$V_2O_5$ (46.4:42.0:0.05:10.0) | $Fe_2O_3$—NiO—$Na_2O$—$V_2O_5$ (36.1:33.8:30.0:0.1) |
| | Calcining temperature (° C.)* | | 800 | 800 |
| | Use quantity (ml) | | 6.5 | 6.5 |
| Reaction condition | Reaction Temperature (° C.) | | 410 | 410 |
| | Feed gas concentration (%) | Benzoic acid | 3.2 | 3.2 |
| | | Water vapor | 80.6 | 80.6 |
| | | Oxygen | 3.2 | 3.2 |
| | | Nitrogen | 12.9 | 12.9 |
| | Space velocity ($h^{-1}$) | | 3400 | 3400 |
| Time after the start of reaction (h) | | | 110 | 110 |
| Reaction result | Conversion of benzoic acid (%) | | 24.0 | 14.0 |
| | Selectivity** | Phenol | 95.5 | 52.5 |
| | | Benzene | 0.8 | 22.7 |
| | | CO, $CO_2$ | 3.6 | 23.4 |
| | Space time yield of phenol (g/l · h) | | 105 | 34 |

*Calcining temperature of $Fe_2O_3$—NiO—$Na_2O$ before supporting $V_2O_5$.
**C-mol %

TABLE 12

| | | | Example 130 | Example 131 |
|---|---|---|---|---|
| Catalyst | Composition (wt. ratio) | | $Fe_2O_3$—NiO—$Na_2O$—$V_2O_5$ (8.3:89.1:0.6:2.0) | $Fe_2O_3$—NiO—$Na_2O$—$V_2O_5$ (20.5:76.9:0.6:2.0) |
| | Calcining temperature (° C.)* | | 800 | 800 |
| | Use quantity (ml) | | 5.5 | 5.5 |
| Reaction condition | Reaction Temperature (° C.) | | 420 | 420 |
| | Feed gas concentration (%) | Benzoic acid | 3.8 | 3.8 |
| | | Water vapor | 76.9 | 76.9 |
| | | Oxygen | 3.8 | 3.8 |
| | | Nitrogen | 15.4 | 15.4 |
| | Space velocity ($h^{-1}$) | | 3400 | 3400 |
| Time after the start of reaction (h) | | | 110 | 110 |
| Reaction result | Conversion of benzoic acid (%) | | 43.6 | 70.5 |
| | Selectivity** | Phenol | 73.4 | 80.9 |
| | | Benzene | 3.3 | 7.1 |
| | | CO, $CO_2$ | 23.0 | 11.8 |
| | Space time yield of phenol (g/l · h) | | 174 | 309 |

| | | | Example 132 | Example 133 |
|---|---|---|---|---|
| Catalyst | Composition (wt. ratio) | | $Fe_2O_3$—NiO—$Na_2O$—$V_2O_5$ (40.5:56.9:0.6:2.0) | $Fe_2O_3$—NiO—$Na_2O$—$V_2O_5$ (59.9:37.5:0.6:2.0) |
| | Calcining temperature (° C.)* | | 800 | 800 |
| | Use quantity (ml) | | 5.5 | 5.5 |

TABLE 12-continued

| | | | | |
|---|---|---|---|---|
| Reaction condition | Reaction Temperature (° C.) | | 420 | 420 |
| | Feed gas concentration (%) | Benzoic acid | 3.8 | 3.8 |
| | | Water vapor | 76.9 | 76.9 |
| | | Oxygen | 3.8 | 3.8 |
| | | Nitrogen | 15.4 | 15.4 |
| | Space velocity ($h^{-1}$) | | 3400 | 3400 |
| Time after the start of reaction (h) | | | 110 | 110 |
| Reaction result | Conversion of benzoic acid (%) | | 87.5 | 95.0 |
| | Selectivity** | Phenol | 90.9 | 82.7 |
| | | Benzene | 3.1 | 15.2 |
| | | CO, $CO_2$ | 1.3 | 0.4 |
| | Space time yield of phenol (g/l · h) | | 431 | 426 |

*Calcining temperature of $Fe_2O_3$—NiO—$Na_2O$ before supporting $V_2O_5$.
**C-mol %

TABLE 13

| | | | Example 134 | Example 135 |
|---|---|---|---|---|
| Catalyst | Composition (wt. ratio) | | $Fe_2O_3$—NiO—$Na_2O$—$V_2O_5$ (78.9:18.5:0.6:2.0) | $Fe_2O_3$—NiO—$Na_2O$—$V_2O_5$ (91.0:6.4:0.6:2.0) |
| | Calcining temperature (° C.)* | | 800 | 800 |
| | Use quantity (ml) | | 5.5 | 5.5 |
| Reaction condition | Reaction Temperature (° C.) | | 420 | 420 |
| | Feed gas concentration (%) | Benzoic acid | 3.8 | 3.8 |
| | | Water vapor | 76.9 | 76.9 |
| | | Oxygen | 3.8 | 3.8 |
| | | Nitrogen | 15.4 | 15.4 |
| | Space velocity ($h^{-1}$) | | 3400 | 3400 |
| Time after the start of reaction (h) | | | 110 | 110 |
| Reaction result | Conversion of benzoic acid (%) | | 99.5 | 100.0 |
| | Selectivity** | Phenol | 71.0 | 60.2 |
| | | Benzene | 22.9 | 38.1 |
| | | CO,$CO_2$ | 4.2 | 0.7 |
| | Space time yield of phenol (g/l · h) | | 383 | 326 |

*Calcining temperature of $Fe_2O_3$—NiO—$Na_2O$ before supporting $V_2O_5$.
**C-mol %

TABLE 14

| | | | Example 136 | Example 137 | Example 138 | Example 139 | Example 140 |
|---|---|---|---|---|---|---|---|
| Catalyst | Composition (wt. ratio) | | $Fe_2O_3$—NiO—$Na_2O$—$V_2O_5$ (50.3:47.1:0.6:2.0) | $Fe_2O_3$—NiO—$Na_2O$—$V_2O_5$ (50.3:47.1:0.6:2.0) | $Fe_2O_3$—NiO—$Na_2O$—$V_2O_5$ (50.3:47.1:0.6:2.0) | $Fe_2O_3$—NiO—$Na_2O$—$V_2O_5$ (50.3:47.1:0.6:2.0) | $Fe_2O_3$—NiO—$Na_2O$—$V_2O_5$ (50.3:47.1:0.6:2.0) |
| | Calcining temperature (° C.)* | | 550 | 600 | 700 | 900 | 950 |
| | Use quantity (ml) | | 5.5 | 5.5 | 5.5 | 5.5 | 5.5 |
| Reaction condition | Reaction Temperature (° C.) | | 420 | 420 | 420 | 420 | 420 |
| | Feed gas concentration (%) | Benzoic acid | 3.8 | 3.8 | 3.8 | 3.8 | 3.8 |
| | | Water vapor | 76.9 | 76.9 | 76.9 | 76.9 | 76.9 |
| | | Oxygen | 3.8 | 3.8 | 3.8 | 3.8 | 3.8 |
| | | Nitrogen | 15.4 | 15.4 | 15.4 | 15.4 | 15.4 |
| | Space velocity ($h^{-1}$) | | 3400 | 3400 | 3400 | 3400 | 3400 |
| Time after the start of reaction (h) | | | 110 | 110 | 110 | 110 | 110 |
| Reaction result | Conversion of benzoic acid (%) | | 100.0 | 100.0 | 99.5 | 55.3 | 6.5 |
| | Selectivity** | Phenol | 33.1 | 60.3 | 70.5 | 91.2 | 74.6 |
| | | Benzene | 25.3 | 20.3 | 13.5 | 2.3 | 14.3 |
| | | CO,$CO_2$ | 40.3 | 16.5 | 12.3 | 6.5 | 11.1 |

TABLE 14-continued

| | | | Example 136 | Example 137 | Example 138 | Example 139 | Example 140 |
|---|---|---|---|---|---|---|---|
| | Space time yield of phenol (g/l · h) | | 179 | 327 | 380 | 273 | 26 |

*Calcining temperature of $Fe_2O_3$—NiO—$Na_2O$ before supporting $V_2O_5$.
**C-mol %

TABLE 15

| | | | Example 141 | Example 142 | Example 143 | Example 144 |
|---|---|---|---|---|---|---|
| Catalyst | Composition (wt. ratio) | | $Fe_2O_3$—NiO—$Na_2O$—$MoO_3$ (49.6:46.4:1.0:3.0) | $Fe_2O_3$—NiO—$Na_2O$—$MoO_3$ (51.0:47.9:1.0:0.1) | $Fe_2O_3$—NiO—$Na_2O$—$MoO_3$ (50.6:47.4:1.0:1.0) | $Fe_2O_3$—NiO—$Na_2O$—$MoO_3$ (50.1:46.9:1.0:2.0) |
| | Calcining temperature (° C.)* | | 800 | 800 | 800 | 800 |
| | Use quantity (ml) | | 5.5 | 5.5 | 5.5 | 5.5 |
| Reaction condition | Reaction Temperature (° C.) | | 420 | 420 | 420 | 420 |
| | Feed gas concentration (%) | Benzoic acid | 3.8 | 3.8 | 3.8 | 3.8 |
| | | Water vapor | 76.9 | 76.9 | 76.9 | 76.9 |
| | | Oxygen | 3.8 | 3.8 | 3.8 | 3.8 |
| | | Nitrogen | 15.4 | 15.4 | 15.4 | 15.4 |
| | Space velocity ($h^{-1}$) | | 2170 | 3400 | 3400 | 3400 |
| Time after the start of reaction (h) | | | 92 | 110 | 110 | 110 |
| Reaction result | Conversion of benzoic acid (%) | | 60.1 | 70.5 | 60.2 | 62.3 |
| | Selectivity** | Phenol | 85.1 | 65.2 | 77.3 | 85.9 |
| | | Benzene | 8.2 | 22.5 | 11.3 | 8.9 |
| | | CO,$CO_2$ | 6.7 | 11.2 | 10.2 | 5.2 |
| | Space time yield of phenol (g/l · h) | | 177 | 249 | 252 | 290 |

*Calcining temperature of $Fe_2O_3$—NiO—$Na_2O$ before supporting $V_2O_5$.
**C-mol %

TABLE 16

| | | | Example 145 | Example 146 | Example 147 |
|---|---|---|---|---|---|
| Catalyst | Composition (wt. ratio) | | $Fe_2O_3$—NiO—$Na_2O$—$MoO_3$ (48.5:45.5:1.0:5.0) | $Fe_2O_3$—NiO—$Na_2O$—$MoO_3$ (47.0:44.0:1.0:8.0) | $Fe_2O_3$—NiO—$Na_2O$—$MoO_3$ (45.9:43.1:1.0:10.0) |
| | Calcining temperature (° C.)* | | 800 | 800 | 800 |
| | Use quantity (ml) | | 5.5 | 5.5 | 5.5 |
| Reaction condition | Reaction Temperature (° C.) | | 420 | 420 | 420 |
| | Feed gas concentration (%) | Benzoic acid | 3.8 | 3.8 | 3.8 |
| | | Water vapor | 76.9 | 76.9 | 76.9 |
| | | Oxygen | 3.8 | 3.8 | 3.8 |
| | | Nitrogen | 15.4 | 15.4 | 15.4 |
| | Space velocity ($h^{-1}$) | | 3400 | 3400 | 3400 |
| Time after the start of reaction (h) | | | 110 | 110 | 110 |
| Reaction result | Conversion of benzoic acid (%) | | 65.4 | 59.2 | 53.6 |
| | Selectivity** | Phenol | 83.6 | 82.3 | 70.6 |
| | | Benzene | 5.7 | 10.4 | 21.6 |
| | | CO,$CO_2$ | 10.4 | 6.9 | 6.9 |
| | Space time yield of phenol (g/l · h) | | 296 | 264 | 205 |

*Calcining temperature of $Fe_2O_3$—NiO—$Na_2O$ before supporting $V_2O_5$.
**C-mol %

TABLE 17

| | | | Example 148 | Example 149 | Example 150 | Example 151 |
|---|---|---|---|---|---|---|
| Catalyst | Composition (wt. ratio) | | $Fe_2O_3$—NiO—$Na_2O$—$MoO_3$ (50.5:46.9: 0.05:3.0) | $Fe_2O_3$—NiO—$Na_2O$—$MoO_3$ (49.9:46.9: 0.2:3.0) | $Fe_2O_3$—NiO—$Na_2O$—$MoO_3$ (49.7:46.7: 0.6:3.0) | $Fe_2O_3$—NiO—$Na_2O$—$MoO_3$ (49.0:46.0: 2.0:3.0) |
| | Calcining temperature (° C.)* | | 800 | 800 | 800 | 800 |
| | Use quantity (ml) | | 5.5 | 5.5 | 5.5 | 5.5 |
| Reaction condition | Reaction Temperature (° C.) | | 420 | 420 | 420 | 420 |
| | Feed gas concentration (%) | Benzoic acid | 3.8 | 3.8 | 3.8 | 3.8 |
| | | Water vapor | 76.9 | 76.9 | 76.9 | 76.9 |
| | | Oxygen | 3.8 | 3.8 | 3.8 | 3.8 |
| | | Nitrogen | 15.4 | 15.4 | 15.4 | 15.4 |
| | Space velocity ($h^{-1}$) | | 3400 | 3400 | 3400 | 3400 |
| Time after the start of reaction (h) | | | 110 | 110 | 110 | 110 |
| Reaction result | Conversion of benzoic acid (%) | | 33.5 | 42.1 | 65.8 | 67.5 |
| | Selectivity** | Phenol | 75.1 | 75.2 | 86.3 | 88.6 |
| | | Benzene | 8.9 | 12.9 | 5.9 | 5.9 |
| | | CO,$CO_2$ | 13.5 | 8.2 | 7.2 | 6.3 |
| | Space time yield of phenol (g/l · h) | | 136 | 172 | 308 | 324 |

*Calcining temperature of $Fe_2O_3$—NiO—$Na_2O$ before supporting $V_2O_5$.
**C-mol %

TABLE 18

| | | | Example 152 | Example 153 | Example 154 |
|---|---|---|---|---|---|
| Catalyst | Composition (wt. ratio) | | $Fe_2O_3$—NiO—$Na_2O$—$MoO_3$ (47.5:44.5: 5.0:3.0) | $Fe_2O_3$—NiO—$Na_2O$—$MoO_3$ (44.9:42.1: 10.0:3.0) | $Fe_2O_3$—NiO—$Na_2O$—$MoO_3$ (34.6:32.4: 30.0:3.0) |
| | Calcining temperature (° C.)* | | 800 | 800 | 800 |
| | Use quantity (ml) | | 5.5 | 5.5 | 5.5 |
| Reaction condition | Reaction Temperature (° C.) | | 410 | 410 | 410 |
| | Feed gas concentration (%) | Benzoic acid | 3.8 | 3.8 | 3.8 |
| | | Water vapor | 76.9 | 76.9 | 76.9 |
| | | Oxygen | 3.8 | 3.8 | 3.8 |
| | | Nitrogen | 15.4 | 15.4 | 15.4 |
| | Space velocity ($h^{-1}$) | | 3400 | 3400 | 3400 |
| Time after the start of reaction (h) | | | 110 | 110 | 100 |
| Reaction result | Conversion of benzoic acid (%) | | 63.5 | 52.3 | 36.9 |
| | Selectivity** | Phenol | 80.6 | 65.8 | 64.5 |
| | | Benzene | 11.4 | 30.3 | 23.8 |
| | | CO,$CO_2$ | 7.2 | 4.2 | 8.3 |
| | Space time yield of phenol (g/l · h) | | 277 | 187 | 129 |

*Calcining temperature of $Fe_2O_3$—NiO—$Na_2O$ before supporting $V_2O_5$.
**C-mol %

TABLE 19

| | | Example 155 | Example 156 | Example 157 | Example 158 | Example 159 |
|---|---|---|---|---|---|---|
| Catalyst | Composition (wt. ratio) | $Fe_2O_3$—NiO—$Na_2O$—$MoO_3$ (50.3:47.1: 0.6:2.0) | $Fe_2O_3$—NiO—$Na_2O$—$MoO_3$ (49.9:45.5: 0.6:4.0) | $Fe_2O_3$—NiO—$Na_2O$—$MoO_3$ (47.5:44.5: 2.0:6.0) | $Fe_2O_3$—NiO—$Na_2O$—$MoO_3$ (46.4:42.0: 0.05:10.0) | $Fe_2O_3$—NiO—$Na_2O$—$MoO_3$ (36.1:33.8: 30.0:0.1) |
| | Calcining temperature (° C.)* | 800 | 800 | 800 | 800 | 800 |
| | Use quantity (ml) | 5.5 | 5.5 | 5.5 | 5.5 | 5.5 |
| Reaction condition | Reaction Temperature (° C.) | 410 | 410 | 410 | 410 | 410 |

TABLE 19-continued

| | | | Example 155 | Example 156 | Example 157 | Example 158 | Example 159 |
|---|---|---|---|---|---|---|---|
| | Feed gas concentration (%) | Benzoic acid | 3.8 | 3.2 | 3.1 | 3.8 | 3.8 |
| | | Water vapor | 76.9 | 80.6 | 78.1 | 76.9 | 76.9 |
| | | Oxygen | 3.8 | 3.2 | 3.1 | 3.8 | 3.8 |
| | | Nitrogen | 15.4 | 12.9 | 12.5 | 15.4 | 15.4 |
| | Space velocity ($h^{-1}$) | | 2180 | 3400 | 3400 | 3400 | 3400 |
| Time after the start of reaction (h) | | | 95 | 100 | 93 | 110 | 110 |
| Reaction result | Conversion of benzoic acid (%) | | 54.2 | 48.5 | 40.3 | 32.0 | 21.0 |
| | Selectivity** | Phenol | 87.8 | 88.1 | 86.3 | 61.2 | 50.2 |
| | | Benzene | 7.9 | 7.5 | 8.1 | 19.5 | 40.3 |
| | | $CO,CO_2$ | 4.3 | 4.4 | 5.6 | 18.5 | 6.5 |
| | Space time yield of phenol (g/l · h) | | 165 | 195 | 154 | 106 | 57 |

*Calcining temperature of $Fe_2O_3$—NiO—$Na_2O$ before supporting $V_2O_5$.
**C-mol %

TABLE 20

| | | | Example 160 | Example 161 | Example 162 | Example 163 |
|---|---|---|---|---|---|---|
| Catalyst | Composition (wt. ratio) | | $Fe_2O_3$—NiO—$Na_2O$—$MoO_3$ (8.3:89.1:0.6:2.0) | $Fe_2O_3$—NiO—$Na_2O$—$MoO_3$ (20.5:76.9:0.6:2.0) | $Fe_2O_3$—NiO—$Na_2O$—$MoO_3$ (40.5:56.9:0.6:2.0) | $Fe_2O_3$—NiO—$Na_2O$—$MoO_3$ (59.9:37.5:0.6:2.0) |
| | Calcining temperature (° C.)* | | 800 | 800 | 800 | 800 |
| | Use quantity (ml) | | 5.5 | 5.5 | 5.5 | 5.5 |
| Reaction condition | Reaction Temperature (° C.) | | 420 | 420 | 420 | 420 |
| | Feed gas concentration (%) | Benzoic acid | 3.8 | 3.8 | 3.8 | 3.8 |
| | | Water vapor | 76.9 | 76.9 | 76.9 | 76.9 |
| | | Oxygen | 3.8 | 3.8 | 3.8 | 3.8 |
| | | Nitrogen | 15.4 | 15.4 | 15.4 | 15.4 |
| | Space velocity ($h^{-1}$) | | 3400 | 3400 | 3400 | 3400 |
| Time after the start of reaction (h) | | | 110 | 110 | 110 | 110 |
| Reaction result | Conversion of benzoic acid (%) | | 29.9 | 40.6 | 50.3 | 76.2 |
| | Selectivity** | Phenol | 80.3 | 86.2 | 89.6 | 83.2 |
| | | Benzene | 2.9 | 7.6 | 3.1 | 10.3 |
| | | $CO,CO_2$ | 11.5 | 5.9 | 5.6 | 6.3 |
| | Space time yield of phenol (g/l · h) | | 130 | 190 | 244 | 343 |

*Calcining temperature of $Fe_2O_3$—NiO—$Na_2O$ before supporting $V_2O_5$.
**C-mol %

TABLE 21

| | | | Example 164 | Example 165 |
|---|---|---|---|---|
| Catalyst | Composition (wt. ratio) | | $Fe_2O_3$—NiO—$Na_2O$—$MoO_3$ (78.9:18.5:0.6:2.0) | $Fe_2O_3$—NiO—$Na_2O$—$MoO_3$ (91.0:6.4:0.6:2.0) |
| | Calcining temperature (° C.)* | | 800 | 800 |
| | Use quantity (ml) | | 5.5 | 5.5 |
| Reaction condition | Reaction Temperature (° C.) | | 420 | 420 |
| | Feed gas concentration (%) | Benzoic acid | 3.8 | 3.8 |
| | | Water vapor | 76.9 | 76.9 |
| | | Oxygen | 3.8 | 3.8 |
| | | Nitrogen | 15.4 | 15.4 |
| | Space velocity ($h^{-1}$) | | 3400 | 3400 |
| Time after the start of reaction (h) | | | 110 | 110 |
| Reaction result | Conversion of benzoic acid (%) | | 88.5 | 95.3 |
| | Selectivity** | Phenol | 74.2 | 55.3 |
| | | Benzene | 12.9 | 22.3 |
| | | $CO,CO_2$ | 10.3 | 20.9 |
| | Space time yield of phenol (g/l · h) | | 356 | 286 |

*Calcining temperature of $Fe_2O_3$—NiO—$Na_2O$ before supporting $V_2O_5$.
**C-mol %

TABLE 22

| | | | Example 166 | Example 167 | Example 168 | Example 169 | Example 170 |
|---|---|---|---|---|---|---|---|
| Catalyst | Composition (wt. ratio) | | $Fe_2O_3$—NiO—$Na_2O$—$MoO_3$ (50.3:47.1: 0.6:2.0) | $Fe_2O_3$—NiO—$Na_2O$—$MoO_3$ (50.3:47.1: 0.6:2.0) | $Fe_2O_3$—NiO—$Na_2O$—$MoO_3$ (50.3:47.1: 0.6:2.0) | $Fe_2O_3$—NiO—$Na_2O$—$MoO_3$ (50.3:47.1: 0.6:2.0) | $Fe_2O_3$—NiO—$Na_2O$—$MoO_3$ (50.3:47.1: 0.6:2.0) |
| | Calcining temperature (° C.)* | | 550 | 600 | 700 | 900 | 950 |
| | Use quantity (ml) | | 5.5 | 5.5 | 5.5 | 5.5 | 5.5 |
| Reaction condition | Reaction Temperature (° C.) | | 420 | 420 | 420 | 420 | 420 |
| | Feed gas concentration (%) | Benzoic acid | 3.8 | 3.8 | 3.8 | 3.8 | 3.8 |
| | | Water vapor | 76.9 | 76.9 | 76.9 | 76.9 | 76.9 |
| | | Oxygen | 3.8 | 3.8 | 3.8 | 3.8 | 3.8 |
| | | Nitrogen | 15.4 | 15.4 | 15.4 | 15.4 | 15.4 |
| | Space velocity ($h^{-1}$) | | 3400 | 3400 | 3400 | 3400 | 3400 |
| Time after the start of reaction (h) | | | 110 | 110 | 110 | 110 | 110 |
| Reaction result | Conversion of benzoic acid (%) | | 100.0 | 98.8 | 90.2 | 43.2 | 8.9 |
| | Selectivity** | Phenol | 61.2 | 62.1 | 70.9 | 86.5 | 72.1 |
| | | Benzene | 15.6 | 13.3 | 8.5 | 6.3 | 14.0 |
| | | CO,$CO_2$ | 22.3 | 16.4 | 21.5 | 3.5 | 11.1 |
| | Space time yield of phenol (g/l · h) | | 331 | 332 | 347 | 202 | 35 |

*Calcining temperature of $Fe_2O_3$—NiO—$Na_2O$ before supporting $V_2O_5$.
**C-mol %

TABLE 23

| | | | Example 171 | Example 172 | Example 173 | Example 174 |
|---|---|---|---|---|---|---|
| Catalyst | Composition (wt. ratio) | | $Fe_2O_3$—NiO—$Na_2O$—$V_2O_5$—$MoO_3$ (49.3:46.2 1.0:2.0:1.5) | $Fe_2O_3$—NiO—$Na_2O$—$V_2O_5$—$MoO_3$ (47.5:44.5 1.0:4.0:3.0) | $Fe_2O_3$—NiO—$Na_2O$—$V_2O_5$—$MoO_3$ (47.5:44.5 2.0:4.0:3.0) | $Fe_2O_3$—NiO—$Na_2O$—$V_2O_5$—$MoO_3$ (50.1:46.9 2.0:0.5:0.5) |
| | Calcining temperature (° C.)* | | 800 | 800 | 800 | 800 |
| | Use quantity (ml) | | 5.5 | 5.5 | 5.5 | 5.5 |
| Reaction condition | Reaction Temperature (° C.) | | 420 | 420 | 420 | 420 |
| | Feed gas concentration (%) | Benzoic acid | 3.8 | 3.8 | 3.8 | 3.8 |
| | | Water vapor | 76.9 | 76.9 | 76.9 | 76.9 |
| | | Oxygen | 3.8 | 3.8 | 3.8 | 3.8 |
| | | Nitrogen | 15.4 | 15.4 | 15.4 | 15.4 |
| | Space velocity ($h^{-1}$) | | 3400 | 3400 | 3400 | 3400 |
| Time after the start of reaction (h) | | | 110 | 110 | 110 | 110 |
| Reaction result | Conversion of benzoic acid (%) | | 83.9 | 88.9 | 95.3 | 62.5 |
| | Selectivity** | Phenol | 93.5 | 94.1 | 88.6 | 80.5 |
| | | Benzene | 3.5 | 4.4 | 2.6 | 15.8 |
| | | CO,$CO_2$ | 1.4 | 0.5 | 8.1 | 5.1 |
| | Space time yield of phenol (g/l · h) | | 425 | 453 | 458 | 273 |

*Calcining temperature of $Fe_2O_3$—NiO—$Na_2O$ before supporting $V_2O_5$.
**C-mol %

TABLE 24

| | | Example 175 | Example 176 | Example 177 | Example 178 |
|---|---|---|---|---|---|
| Catalyst | Composition (wt. ratio) | $Fe_2O_3$—NiO—$Na_2O$—$V_2O_5$—$MoO_3$ (50.5:47.3 2.0:0.1:0.1) | $Fe_2O_3$—NiO—$Na_2O$—$V_2O_5$—$MoO_3$ (45.4:42.6 2:5:5) | $Fe_2O_3$—NiO—$Na_2O$—$V_2O_5$—$MoO_3$ (40.2:37.8 2:10:10) | $Fe_2O_3$—NiO—$Na_2O$—$V_2O_5$—$MoO_3$ (25.8:24.2 30:10:10) |
| | Calcining temperature (° C.)* | 800 | 800 | 800 | 800 |
| | Use quantity (ml) | 5.5 | 5.5 | 5.5 | 5.5 |

TABLE 24-continued

| | | | Example 175 | Example 176 | Example 177 | Example 178 |
|---|---|---|---|---|---|---|
| Reaction condition | Reaction Temperature (° C.) | | 420 | 420 | 420 | 420 |
| | Feed gas concentration (%) | Benzoic acid | 3.8 | 3.8 | 3.8 | 3.8 |
| | | Water vapor | 76.9 | 76.9 | 76.9 | 76.9 |
| | | Oxygen | 3.8 | 3.8 | 3.8 | 3.8 |
| | | Nitrogen | 15.4 | 15.4 | 15.4 | 15.4 |
| | Space velocity ($h^{-1}$) | | 3400 | 3400 | 3400 | 3400 |
| Time after the start of reaction (h) | | | 110 | 110 | 110 | 110 |
| Reaction result | Conversion of benzoic acid (%) | | 44.3 | 77.7 | 85.4 | 55.5 |
| | Selectivity** | Phenol | 71.5 | 84.3 | 89.8 | 51.0 |
| | | Benzene | 21.1 | 8.4 | 3.3 | 15.4 |
| | | $CO,CO_2$ | 5.9 | 5.6 | 5.0 | 31.8 |
| | Space time yield of phenol (g/l · h) | | 172 | 355 | 416 | 153 |

*Calcining temperature of $Fe_2O_3$—NiO—$Na_2O$ before supporting $V_2O_5$.
**C-mol %

TABLE 25

| | | | Example 179 | Example 180 |
|---|---|---|---|---|
| Catalyst | Composition (wt. ratio) | | $Fe_2O_3$—NiO—$Na_2O$—$V_2O_5$—$MoO_3$ (51.5:48.3 0.05:0.1:0.1) | $Fe_2O_3$—NiO—$Na_2O$—$V_2O_5$—$MoO_3$ (45.4:42.6 1:10:1) |
| | Calcining temperature (° C.)* | | 800 | 800 |
| | Use quantity (ml) | | 5.5 | 5.5 |
| Reaction condition | Reaction Temperature (° C.) | | 420 | 420 |
| | Feed gas concentration (%) | Benzoic acid | 3.8 | 3.8 |
| | | Water vapor | 76.9 | 76.9 |

TABLE 25-continued

| | | | Example 179 | Example 180 |
|---|---|---|---|---|
| | | Oxygen | 3.8 | 3.8 |
| | | Nitrogen | 15.4 | 15.4 |
| | Space velocity ($h^{-1}$) | | 3400 | 3400 |
| Time after the start of reaction (h) | | | 110 | 110 |
| Reaction result | Conversion of benzoic acid (%) | | 35.1 | 55.9 |
| | Selectivity** | Phenol | 76.6 | 86.1 |
| | | Benzene | 12.9 | 7.4 |
| | | $CO,CO_2$ | 10.0 | 4.6 |
| | Space time yield of phenol (g/l · h) | | 146 | 261 |

*Calcining temperature of $Fe_2O_3$—NiO—$Na_2O$ before supporting $V_2O_5$.
**C-mol %

TABLE 26

| | | | Example 181 | Example 182 | Example 183 | Example 184 |
|---|---|---|---|---|---|---|
| Catalyst | Composition (wt. ratio) | | $Fe_2O_3$—NiO—$K_2O$—$V_2O_5$ (50.3:47.1: 0.6:2.0) | $Fe_2O_3$—NiO—$Li_2O$—$V_2O_5$ (50.3:47.1: 0.6:2.0) | $Fe_2O_3$—NiO—$Rb_2O$—$V_2O_5$ (50.3:47.1: 0.6:2.0) | $Fe_2O_3$—NiO—$Cs_2O$—$V_2O_5$ (50.3:47.1: 0.6:2.0) |
| | Calcining temperature (° C.)* | | 800 | 800 | 800 | 800 |
| | Use quantity (ml) | | 5.5 | 5.5 | 5.5 | 5.5 |
| Reaction condition | Reaction Temperature (° C.) | | 420 | 420 | 420 | 420 |
| | Feed gas concentration (%) | Benzoic acid | 3.8 | 3.8 | 3.8 | 3.8 |
| | | Water vapor | 76.9 | 76.9 | 76.9 | 76.9 |
| | | Oxygen | 3.8 | 3.8 | 3.8 | 3.8 |
| | | Nitrogen | 15.4 | 15.4 | 15.4 | 15.4 |
| | Space velocity ($h^{-1}$) | | 3400 | 3400 | 3400 | 3400 |
| Time after the start of reaction (h) | | | 110 | 110 | 110 | 110 |
| Reaction result | Conversion of benzoic acid (%) | | 85.9 | 66.8 | 54.3 | 44.3 |
| | Selectivity** | Phenol | 90.6 | 90.1 | 83.6 | 70.6 |

TABLE 26-continued

| | | | Example 181 | Example 182 | Example 183 | Example 184 |
|---|---|---|---|---|---|---|
| | | Benzene | 5.4 | 3.3 | 7.5 | 16.3 |
| | | $CO,CO_2$ | 2.3 | 6.4 | 8.5 | 10.3 |
| | Space time yield of phenol (g/l · h) | | 422 | 326 | 246 | 170 |

*Calcining temperature of $Fe_2O_3$—NiO—$Na_2O$ before supporting $V_2O_5$.
**C-mol %

TABLE 27

| | | | Example 185 | Example 186 | Example 187 | Example 188 |
|---|---|---|---|---|---|---|
| Catalyst | Composition (wt. ratio) | | $Fe_2O_3$—NiO—$Na_2O$—$V_2O_5$—$MoO_3$ (49.3:46.2 1.0:2.0:1.5) | $Fe_2O_3$—NiO—$Na_2O$—$V_2O_5$ (50.3:47.1: 0.6:2.0) | $Fe_2O_3$—NiO—$Na_2O$—$V_2O_5$ (50.3:47.1: 0.6:2.0) | $Fe_2O_3$—NiO—$Na_2O$—$V_2O_5$ (50.3:47.1: 0.6:2.0) |
| | Use quantity (ml) | | 5.5 | 5.5 | 5.5 | 5.5 |
| Reaction condition | Reaction Temperature (° C.) | | 420 | 420 | 420 | 420 |
| | Feed gas concentration (%) | Benzoic acid | 3.8 | 3.8 | 3.8 | 3.8 |
| | | Water vapor | 76.9 | 76.9 | 76.9 | 76.9 |
| | | Oxygen | 3.8 | 3.8 | 3.8 | 3.8 |
| | | Nitrogen | 15.4 | 15.4 | 15.4 | 15.4 |
| | Space velocity ($h^{-1}$) | | 3400 | 3400 | 3400 | 3400 |
| Time after the start of reaction (h) | | | 110 | 110 | 110 | 110 |
| Reaction result | Conversion of benzoic acid (%) | | 94.9 | 65.9 | 41.3 | 31.5 |
| | Selectivity** | Phenol | 93.2 | 96.3 | 98.0 | 80.0 |
| | | Benzene | 5.3 | 1.2 | 1.0 | 13.2 |
| | | $CO,CO_2$ | 1.1 | 1.3 | 0.6 | 5.4 |
| | Space time yield of phenol (g/l · h) | | 480 | 344 | 219 | 137 |

TABLE 28

| | | | Example 189 | Example 190 | Example 191 | Example 192 |
|---|---|---|---|---|---|---|
| Catalyst | Composition (wt. ratio) | | $Fe_2O_3$—NiO—MgO—$V_2O_5$ (50.3:47.1: 0.6:2.0) | $Fe_2O_3$—NiO—CaO—$V_2O_5$ (50.3:47.1: 0.6:2.0) | $Fe_2O_3$—NiO—SrO—$V_2O_5$ (50.3:47.1: 0.6:2.0) | $Fe_2O_3$—NiO—BaO—$V_2O_5$ (50.3:47.1: 0.6:2.0) |
| | Calcining temperature (° C.)* | | 800 | 800 | 800 | 800 |
| | Use quantity (ml) | | 5.5 | 5.5 | 5.5 | 5.5 |
| Reaction condition | Reaction Temperature (° C.) | | 420 | 400 | 300 | 500 |
| | Feed gas concentration (%) | Benzoic acid | 3.8 | 3.8 | 3.8 | 3.8 |
| | | Water vapor | 76.9 | 76.9 | 76.9 | 76.9 |
| | | Oxygen | 3.8 | 3.8 | 3.8 | 3.8 |
| | | Nitrogen | 15.4 | 15.4 | 15.4 | 15.4 |
| | Space velocity ($h^{-1}$) | | 2150 | 3400 | 3400 | 3400 |
| Time after the start of reaction (h) | | | 110 | 110 | 110 | 110 |
| Reaction result | Conversion of benzoic acid (%) | | 63.5 | 55.3 | 43.2 | 50.3 |
| | Selectivity** | Phenol | 90.3 | 90.4 | 89.3 | 88.8 |
| | | Benzene | 2.3 | 5.1 | 1.5 | 10.2 |
| | | $CO,CO_2$ | 7.3 | 3.8 | 8.1 | 1.3 |
| | Space time yield of phenol (g/l · h) | | 196 | 271 | 209 | 242 |

*Calcining temperature of $Fe_2O_3$—NiO—$Na_2O$ before supporting $V_2O_5$.
**C-mol %

TABLE 29

| | | | Example 193 | Example 194 | Example 195 |
|---|---|---|---|---|---|
| Catalyst | Composition (wt. ratio) | | $Fe_2O_3$—NiO—MgO—$MoO_3$ (49.6:46.4: 1.0:3.0) | $Fe_2O$—NiO—CaO—$MoO_3$ (51.0:47.9: 1.0:0.1) | $Fe_2O_3$—NiO—BaO—$MoO_3$ (50.6:47.4: 1.0:1.0) |
| | Use quantity (ml) | | 5.5 | 5.5 | 5.5 |
| Reaction condition | Alkyl benzoic acid group as raw material | | o-toluic acid | o-toluic acid | o-toluic acid |
| | Reaction Temperature (° C.) | | 420 | 420 | 420 |
| | Feed gas concentration (%) | Alkyl benzoic acid | 3.8 | 3.8 | 3.8 |
| | | Water vapor | 76.9 | 76.9 | 76.9 |
| | | Oxygen | 3.8 | 3.8 | 3.8 |
| | | Nitrogen | 15.4 | 15.4 | 15.4 |
| | Space velocity ($h^{-1}$) | | 3400 | 3400 | 3400 |
| Time after the start of reaction (h) | | | 110 | 110 | 110 |
| Reaction result | Conversion of raw material (%) | | 59.6 | 42.5 | 40.3 |
| | Selectivity** | Alkyl phenol group | 70.2 (m-cresol) | 66.6 (m-cresol) | 72.2 (m-cresol) |
| | | CO,$CO_2$ | 11.6 | 13.5 | 10.2 |
| | Space time yield of phenol (g/l · h) | | 261 | 177 | 181 |

**C-mol %

TABLE 30

| | | | Comparative example 4 | Comparative example 5 | Comparative example 6 |
|---|---|---|---|---|---|
| Catalyst | Composition (wt. ratio) | | $Fe_2O_3$—NiO—$Na_2O$ (51.3:48.1:0.6) | $MoO_3$—$V_2O_5$—CuO—$Na_2O$—$Al_2O_3$ (3.9:3.7:3.8:5.9:82.7) | CuO—ZnO—$K_2O$—$Al_2O_3$ (4.0:3.0:3.6:89.4) |
| | Use quantity (ml) | | 6.5 | 5.9 | 5.3 |
| Reaction condition | Reaction Temperature (° C.) | | 410 | 300 | 300 |
| | Feed gas concentration (%) | Benzoic acid | 2.7 | 2.3 | 2.3 |
| | | Water vapor | 69.4 | 69.9 | 69.9 |
| | | Oxygen | 5.6 | 4.7 | 4.7 |
| | | Nitrogen | 22.2 | 23.1 | 23.1 |
| | Space velocity ($h^{-1}$) | | 3950 | 2640 | 2960 |
| Time after the start of reaction (h) | | | 91 | 83 | 87 |
| Reaction result | Conversion of benzoic acid (%) | | 31.2 | 35.6 | 12.2 |
| | Selectivity** | Phenol | 24.0 | 51.9 | 26.3 |
| | | Benzene | 38.9 | 18.7 | 53.6 |
| | | CO,$CO_2$ | 36.7 | 29.4 | 20.1 |
| | Space time yield of phenol (g/l · h) | | 21 | 47 | 9 |

**C-mol %

TABLE 31

| | | Example 196 | Comparative example 7 | Comparative example 8 |
|---|---|---|---|---|
| Catalyst | Composition (wt. ratio) | $Fe_2O_3$—NiO—$Na_2O$—$V_2O_5$—$MoO_3$ (49.3:46.2 1.0:2.0:1.5) | $MoO_3$—$V_2O_5$—CuO—$Na_2O$—$Al_2O_3$ (3.9:3.7:3.8: 5.9:82.7) :0.6:2.0) | CuO—ZnO—$K_2O$—$Al_2O_3$ (4.0:3.0:3.6: 89.4) :0.6:2.0) |
| | Use quantity (ml) | 5.5 | 5.5 | 5.5 |
| Reaction | Alkyl benzoic acid group | o-toluic acid | o-toluic acid | o-toluic acid |

TABLE 31-continued

| | | | Example 196 | Comparative example 7 | Comparative example 8 |
|---|---|---|---|---|---|
| condition | as raw material | | | | |
| | Reaction Temperature (° C.) | | 420 | 300 | 300 |
| | Feed gas concentration (%) | Alkyl benzoic acid | 3.8 | 3.8 | 3.8 |
| | | Water vapor | 76.9 | 76.9 | 76.9 |
| | | Oxygen | 3.8 | 3.8 | 3.8 |
| | | Nitrogen | 15.4 | 15.4 | 15.4 |
| | Space velocity ($h^{-1}$) | | 3400 | 3400 | 3400 |
| Time after the start of reaction (h) | | | 110 | 110 | 110 |
| Reaction result | Conversion of raw material (%) | | 42.5 | 23.5 | 11.5 |
| | Selectivity** | Alkyl phenol group | 63.2 (m-cresol) | 2.8 (m-cresol) | 1.9 (m-cresol) |
| | | $CO,CO_2$ | 10.9 | 28.9 | 31.6 |
| | Space time yield of phenol (g/l · h) | | 167 | 4 | 1 |

**C-mol %

What is claimed is:

1. A method for producing phenols using a catalyst, from benzoic acid or an alkyl benzoic acid, the catalyst for producing phenols consisting essentially of;

an iron oxide;

a nickel oxide;

at least one first oxide selected from the group consisting of a vanadium oxide and a molybdenum oxide; and at least one second oxide selected from the group consisting of an alkali metal oxide and an alkaline earth metal oxide;

said method comprising reacting a benzoic acid or an alkyl benzoic acid with oxygen and water vapor.

2. The method of claim 1 wherein said catalyst consists essentially of;

an iron oxide;

a nickel oxide;

at least one first oxide selected from the group consisting of a vanadium oxide and a molybdenum oxide, said vanadium oxide being $V_2O_4$ or $V_2O_5$ and said molybdenum oxide being $MoO_2$ or $MoO_3$, the catalyst containing the vanadium oxide in an amount of 0.1 to 10 wt. % and molybdenum oxide in an amount of 0.5 to 5 wt. %; and at least one second oxide selected from the group consisting of an alkali metal oxide and an alkaline earth metal oxide, said alkali metal oxide being $Li_2O$, $Na_2O$, $K_2O$, $Rb_2O$ or $Cs_2O$ and said alkaline earth metal oxide being MgO, CaO, SrO or BaO, the catalyst containing the alkali metal oxide in an amount of 0.05 to 30 wt. % and the alkaline earth metal oxide in an amount of 0.05 to 30 wt. %.

3. The method of claim 1, wherein the oxygen amount is from 0.5 to 50 mole fold to the benzoic acid or alkyl benzoic acid.

4. The method of claim 1, wherein water vapor amount is from 1 to 100 mole fold to the benzoic acid or alkyl benzoic acid.

5. The method of claim 1, wherein said alkyl benzoic acid has an alkyl group with 1 to 8 carbon atoms on ortho-, meta-, or para-position.

6. The method of claim 5, wherein said alkyl benzoic acid has an alkyl group with 1 to 5 carbon atoms on ortho-, meta-, or para-position.

7. The method of claim 1, wherein said reaction is performed at a space velocity of 100 to 50000 $hr^{-1}$.

8. The method of claim 7, wherein said reaction is performed at a temperature of 200 to 600° C.

9. The method of claim 8, wherein said temperature is from 300 to 500° C.

10. The method of claim 1, wherein said reaction is performed at a temperature of 200 to 600° C.

11. The method of claim 10, wherein said temperature is from 300 to 500° C.

12. The method of claim 1, wherein the molybdenum oxide is $MoO_2$ or $MoO_3$.

13. The method of claim 1 wherein the first oxide is $MoO_2$ or $MoO_3$.

14. The method of claim 11, wherein the molybdenum oxide is $MoO_2$ or $MoO_3$.

15. The method of claim 11 wherein the first oxide is $MoO_2$ or $MoO_3$.

16. The method of claim 1 wherein the ratio of nickel oxide as NiO to iron oxide as $Fe_2O_3$ in the catalyst is 0.1 to 10.0 by weight.

17. The method of claim 2 wherein the ratio of nickel oxide as NiO to iron oxide as $Fe_2O_3$ in the catalyst is 0.1 to 10.0 by weight.

* * * * *